(12) United States Patent
Bowen et al.

(10) Patent No.: US 11,154,669 B2
(45) Date of Patent: Oct. 26, 2021

(54) WICKLESS VAPORIZING DEVICES AND METHODS

(71) Applicant: JUUL Labs, Inc., San Francisco, CA (US)

(72) Inventors: Adam Bowen, San Francisco, CA (US); Ariel Atkins, San Francisco, CA (US); Alexander J. Gould, San Francisco, CA (US); Carlos Schuler, San Francisco, CA (US); Bradley J. Ingebrethsen, San Francisco, CA (US)

(73) Assignee: JUUL Labs, Inc., San Francisco, CA (US)

( * ) Notice: Subject to any disclaimer, the term of this patent is extended or adjusted under 35 U.S.C. 154(b) by 330 days.

(21) Appl. No.: 15/743,274

(22) PCT Filed: Jul. 11, 2016

(86) PCT No.: PCT/US2016/041819
§ 371 (c)(1),
(2) Date: Jan. 9, 2018

(87) PCT Pub. No.: WO2017/011419
PCT Pub. Date: Jan. 19, 2017

(65) Prior Publication Data
US 2018/0199627 A1    Jul. 19, 2018

Related U.S. Application Data

(60) Provisional application No. 62/191,307, filed on Jul. 10, 2015.

(51) Int. Cl.
*A24F 47/00* (2020.01)
*A61M 15/06* (2006.01)
(Continued)

(52) U.S. Cl.
CPC ........... *A61M 15/06* (2013.01); *A24B 15/167* (2016.11); *A24D 3/17* (2020.01); *A24F 3/02* (2013.01);
(Continued)

(58) Field of Classification Search
CPC ....................................................... A24F 47/00
(Continued)

(56) References Cited

U.S. PATENT DOCUMENTS 4,945,931 A    8/1990 Gori
5,666,977 A    9/1997 Higgins et al.
(Continued)

FOREIGN PATENT DOCUMENTS

CN    1323231 A    11/2001
CN    1541577 A    11/2004
(Continued)

*Primary Examiner* — Phuong K Dinh
(74) *Attorney, Agent, or Firm* — Mintz Levin Cohn Ferris Glovsky and Popeo, P.C.

(57) ABSTRACT

Deformable valves and atomizer designs for a vaporizer (e.g., electronic cigarette). The vaporizer may be used for vaporization of liquid and/or organic material. The vaporizer may enable enhanced flow control of fluid and may generate high quality and quantity of vapor efficiently. In some instances, flow path of the vaporizer may allow bulk fluid flow, e.g., in contrast to capillary flow, to deliver fluid to a vicinity of the vaporizer. In some instances, the vaporizer may utilize improved atomizer designs for vaporizing devices, where said designs can be configured optionally, with various embodiments of a breath-modulating deformable valve.

38 Claims, 17 Drawing Sheets

(51) Int. Cl.
*A61M 11/00* (2006.01)
*A61M 11/04* (2006.01)
*H05B 1/02* (2006.01)
*A61M 15/00* (2006.01)
*A24D 3/17* (2020.01)
*A24F 40/46* (2020.01)
*A24F 40/48* (2020.01)
*A24F 40/485* (2020.01)
*A24F 40/50* (2020.01)
*A24F 40/85* (2020.01)
*A61M 16/00* (2006.01)
*A24B 15/167* (2020.01)
*A24F 3/02* (2006.01)
*A24F 7/04* (2006.01)
*A61M 11/08* (2006.01)
*F16K 15/18* (2006.01)
*F16K 31/00* (2006.01)
*A24F 40/10* (2020.01)

(52) U.S. Cl.
CPC ............... *A24F 7/04* (2013.01); *A24F 40/46* (2020.01); *A24F 40/48* (2020.01); *A24F 40/485* (2020.01); *A24F 40/50* (2020.01); *A24F 40/85* (2020.01); *A61M 11/003* (2014.02); *A61M 11/007* (2014.02); *A61M 11/042* (2014.02); *A61M 11/08* (2013.01); *A61M 15/0093* (2014.02); *A61M 16/0003* (2014.02); *F16K 15/185* (2013.01); *F16K 31/002* (2013.01); *H05B 1/0227* (2013.01); *H05B 1/0297* (2013.01); *A24F 40/10* (2020.01); *A61M 2016/0024* (2013.01); *A61M 2205/075* (2013.01); *A61M 2205/13* (2013.01); *A61M 2205/3334* (2013.01); *A61M 2205/3368* (2013.01); *A61M 2205/3653* (2013.01); *A61M 2205/502* (2013.01); *A61M 2205/7536* (2013.01); *A61M 2206/20* (2013.01)

(58) Field of Classification Search
USPC .................................................. 131/328–329
See application file for complete search history.

(56) References Cited

U.S. PATENT DOCUMENTS

| | | | |
|---|---|---|---|
| 6,234,167 B1 | 5/2001 | Cox et al. | |
| 8,314,591 B2 | 11/2012 | Terry et al. | |
| 9,095,175 B2 | 8/2015 | Terry et al. | |
| 9,247,773 B2 | 2/2016 | Memari et al. | |
| 9,271,529 B2 | 3/2016 | Alima | |
| 9,555,203 B2 | 1/2017 | Terry et al. | |
| 9,668,522 B2 | 6/2017 | Memari et al. | |
| 1,003,932 A1 | 8/2018 | Verleur et al. | |
| 1,005,812 A1 | 8/2018 | Monsees et al. | |
| 1,009,271 A1 | 10/2018 | Terry et al. | |
| 1,015,927 A1 | 12/2018 | Minskoff et al. | |
| 1,027,993 A1 | 5/2019 | Christensen et al. | |
| 1,030,022 A1 | 5/2019 | Terry et al. | |
| 1,038,336 A1 | 8/2019 | Larson | |
| 2007/0283972 A1 | 12/2007 | Monsees et al. | |
| 2009/0095311 A1 | 4/2009 | Han | |
| 2009/0293892 A1* | 12/2009 | Williams | A24F 47/008 131/328 |
| 2011/0277761 A1 | 11/2011 | Terry et al. | |
| 2011/0277780 A1 | 11/2011 | Terry et al. | |
| 2012/0230659 A1 | 9/2012 | Goodman et al. | |
| 2013/0056013 A1 | 3/2013 | Terry et al. | |
| 2014/0034563 A1 | 2/2014 | Yotani | |
| 2014/0041658 A1 | 2/2014 | Goodman et al. | |
| 2014/0109921 A1 | 4/2014 | Chen | |
| 2014/0190501 A1 | 7/2014 | Liu | |
| 2015/0027470 A1* | 1/2015 | Kane | A24F 47/008 131/329 |
| 2015/0114410 A1 | 4/2015 | Doster | |
| 2015/0142387 A1 | 5/2015 | Alarcon et al. | |
| 2015/0157054 A1 | 6/2015 | Liu | |
| 2015/0217068 A1 | 8/2015 | Wakalopulos | |
| 2015/0245654 A1 | 9/2015 | Memari et al. | |
| 2015/0245655 A1 | 9/2015 | Memari et al. | |
| 2015/0245657 A1 | 9/2015 | Memari et al. | |
| 2015/0245665 A1 | 9/2015 | Memari et al. | |
| 2015/0245666 A1 | 9/2015 | Memari et al. | |
| 2015/0245667 A1 | 9/2015 | Memari et al. | |
| 2015/0245668 A1 | 9/2015 | Memari et al. | |
| 2015/0282530 A1 | 10/2015 | Johnson et al. | |
| 2015/0327596 A1* | 11/2015 | Alarcon | H04L 67/22 131/328 |
| 2015/0351456 A1 | 12/2015 | Johnson et al. | |
| 2016/0150824 A1 | 6/2016 | Memari et al. | |
| 2016/0174611 A1 | 6/2016 | Monsees et al. | |
| 2016/0286865 A1 | 10/2016 | King et al. | |
| 2016/0338412 A1* | 11/2016 | Monsees | A24F 47/008 |
| 2016/0360786 A1 | 12/2016 | Bellinger et al. | |
| 2016/0366725 A1 | 12/2016 | Tucker et al. | |
| 2017/0042242 A1 | 2/2017 | Hon | |
| 2017/0156398 A1 | 6/2017 | Sur et al. | |
| 2017/0208864 A1 | 7/2017 | Anderson, Jr. et al. | |
| 2017/0231286 A1 | 8/2017 | Borkovec et al. | |
| 2017/0238617 A1 | 8/2017 | Scatterday | |
| 2018/0064169 A1 | 3/2018 | Biel et al. | |
| 2018/0080559 A1 | 3/2018 | Li et al. | |
| 2018/0103685 A1 | 4/2018 | Yener | |
| 2018/0220707 A1 | 8/2018 | Biel et al. | |
| 2019/0256231 A1 | 8/2019 | Atkins et al. | |

FOREIGN PATENT DOCUMENTS

| | | |
|---|---|---|
| CN | 101282660 A | 10/2008 |
| CN | 103501847 A | 1/2014 |
| CN | 104023574 A | 9/2014 |
| EP | 1618803 A1 | 1/2006 |
| EP | 3085257 A1 | 10/2016 |
| EP | 3313215 B1 | 6/2019 |
| EP | 3409597 B1 | 6/2019 |
| JP | 2006-524494 A | 11/2006 |
| JP | 2009-502136 A | 1/2009 |
| JP | 2009-22752 A | 2/2009 |
| JP | 2014-525237 A | 9/2014 |
| JP | 2015-504653 A | 2/2015 |
| JP | 2017-127649 A | 7/2017 |
| WO | WO-97/42993 A2 | 11/1997 |
| WO | WO-2003061716 A1 | 7/2003 |
| WO | WO-2005/106350 A2 | 11/2005 |
| WO | WO-2007/012007 A2 | 1/2007 |
| WO | WO-2011/117580 A2 | 9/2011 |
| WO | WO-2011146174 A2 | 11/2011 |
| WO | WO-2013/098411 A1 | 7/2013 |
| WO | WO-2014-012907 A1 | 1/2014 |
| WO | WO-2014/150573 A2 | 9/2014 |
| WO | WO-2015/013109 A1 | 1/2015 |
| WO | WO-2015/013126 A2 | 1/2015 |
| WO | WO-2016108694 A1 | 7/2016 |
| WO | WO-2016193336 A1 | 12/2016 |
| WO | WO-2016200382 A1 | 12/2016 |
| WO | WO-2016207357 A1 | 12/2016 |
| WO | WO-2017036819 A1 | 3/2017 |
| WO | WO-2017055564 A1 | 4/2017 |
| WO | WO-2017060279 A1 | 4/2017 |
| WO | WO-2017064323 A1 | 4/2017 |
| WO | WO-2017121546 A1 | 7/2017 |
| WO | WO-2017137554 A1 | 8/2017 |
| WO | WO-2017163052 A1 | 9/2017 |

* cited by examiner

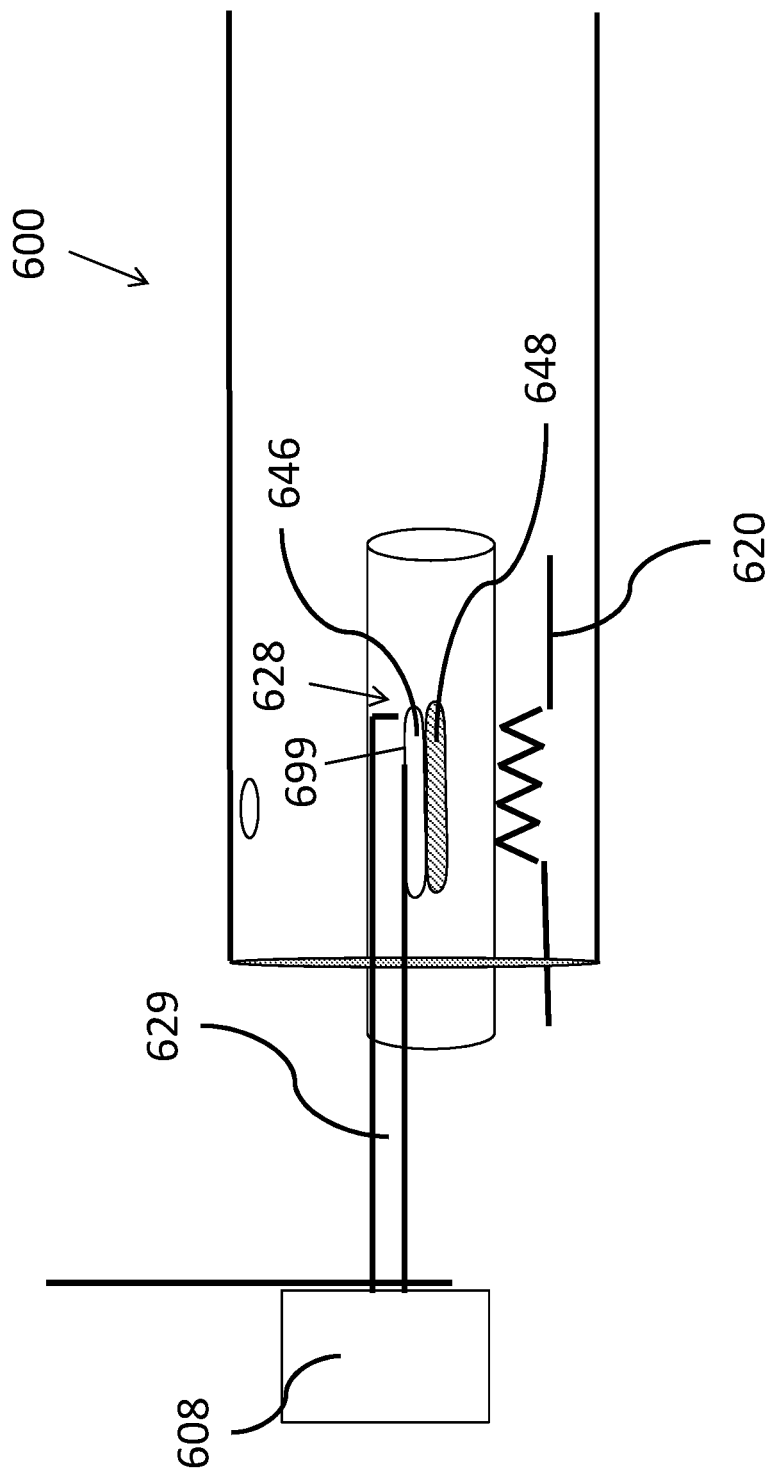

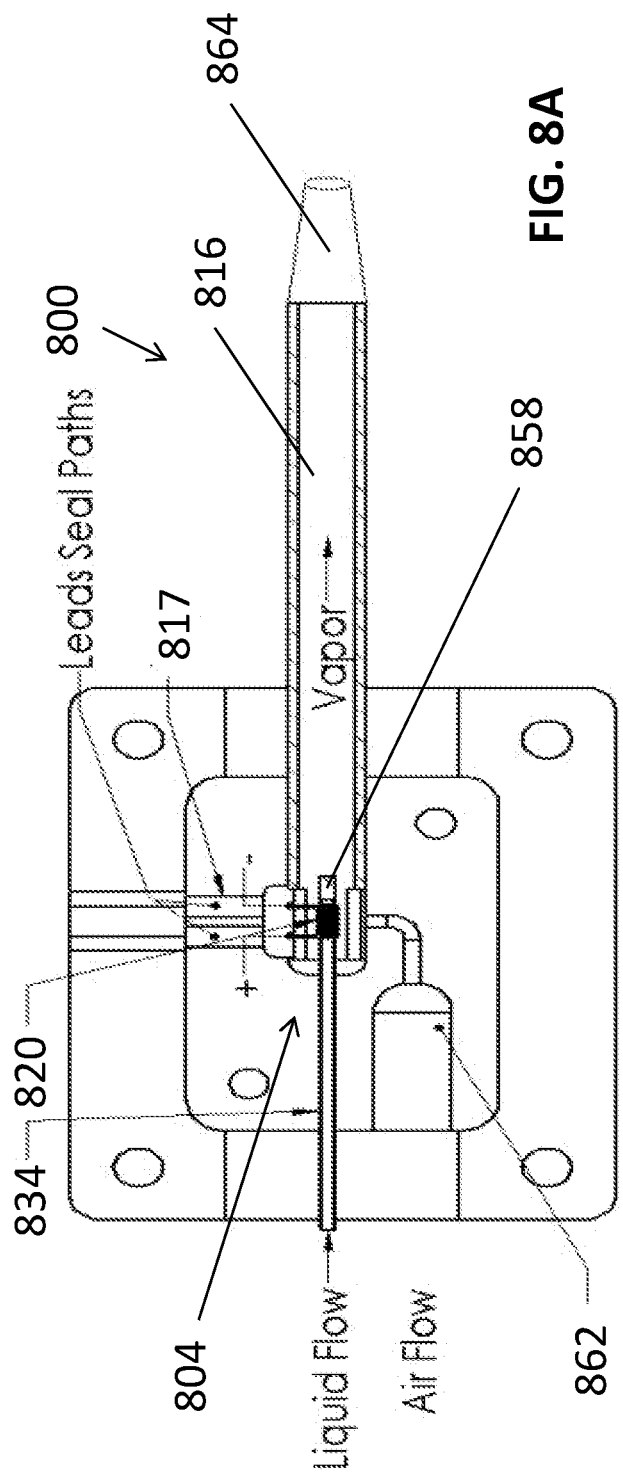
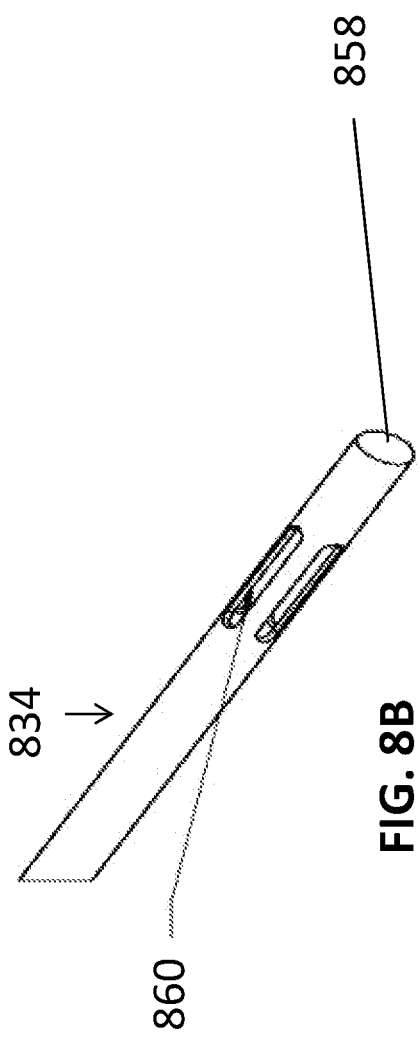
FIG. 8A
FIG. 8B

WICKLESS VAPORIZING DEVICES AND METHODS

CROSS REFERENCE TO RELATED APPLICATIONS

This application claims priority to U.S. Provisional Patent Application No. 62/191,307, filed Jul. 10, 2015, titled "WICKLESS VAPORIZING DEVICES AND METHODS," the entirety of which is incorporated by reference herein.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Vaporizing devices (e.g., electronic cigarette devices, e-cigarettes, e-cigs, etc.) of wide ranging capabilities have been developed in response to a rising demand for alternatives to conventional tobacco products. In general, vaporizing devices are portable and self-contained electrically driven devices that may be used for vaporization of liquid and/or organic products. For example, a vaporizing device may utilize heat to vaporize or transform a propylene glycol (PG) or vegetable glycerin (VG) based liquid solution into an aerosol for inhalation. In some instances, a vaporizing device may produce a mist or aerosol bearing a physical sensation, appearance, and/or flavor similar to that of smoke produced from tobacco.

Existing vaporizing devices include several limitations. For example, existing vaporizing devices may comprise configurations that inevitably lead to poor user experience due to issues related to flooding, cooked or burnt flavor, flavor crossover, and/or short battery life. Moreover, existing vaporizing devices may lack an ability to modulate or control a flow of liquid therethrough. Such problems may be related to the use of a wick, and/or the buildup of material on the heating components (e.g., atomizer, heater, etc.).

A need exists for improved vaporizing devices configured for drawing and vaporizing a fluid that are efficient and provide high quality vapor. Described herein are apparatuses (devices and systems) and method that may address these limitations.

SUMMARY

Embodiments disclosed herein provide devices, systems, and methods for drawing and vaporizing a fluid. In many instances, vaporizing devices may be utilized to generate vapor. The vaporizing device may vaporize a liquid without combusting an aerosolizable material. The vaporizing device may comprise a valve and/or an improved atomizer. In some instances, the vaporizing device as described herein may comprise a wickless vaporizing device with a breath-modulated liquid flow control. The breath-modulated liquid flow control may be a breath-modulated valve. In some instances, the vaporizing device may comprise atomizers comprising a tube and a heating element (heater). The valve and/or improved atomizer may improve a vaporization quality, enhance flow control and/or efficiency of the device.

For example, described herein are hand-held vaporizer apparatuses that may include: an elongate body; a reservoir configured to contain a vaporizable fluid; an atomizer within the elongate body configured to form a vapor from the vaporizable fluid, the atomizer comprising: a heating element; and an inner elongate tube extending between the reservoir and the heating element; and a flow modulator configured to modulate flow of the fluid through the inner elongate tube from the reservoir to the heating element.

Any of these hand-held vaporizer apparatuses may be wickless hand-held vaporizer apparatuses, and may include: an elongate body having a mouthpiece; a reservoir configured to contain a vaporizable fluid; a wickless atomizer within the elongate body configured to form a vapor from the vaporizable fluid, the atomizer comprising: a heater; and an inner elongate tube extending between the reservoir and the heater configured to permit bulk flow of the vaporizable fluid from the reservoir to the heater; a flow modulator configured to modulate flow of the fluid through the inner elongate tube from the reservoir to the heater; a draw sensor configured to detect a user drawing on the mouthpiece; and a controller configured to control the flow modulator to allow bulk flow of vaporizable fluid when the user is drawing on the mouthpiece.

For example, a hand-held vaporizer may include: a cartridge comprising a reservoir configured to contain a fluid; an atomizer configured to form a vapor from the fluid; a flow path comprising a first portion originating in the reservoir and continuing to atomizer, and a second portion of the flow path positioned to deliver the vapor from the atomizer to an outlet of the vaporizer; and a valve comprising an open configuration and a closed configuration wherein the valve is configured to modulate a flow of fluid within the first portion of the flow path. In some embodiments, a primary means of fluid transportation through the first portion of the flow path is not via capillary action. In some embodiments, the primary means of fluid transportation through the first portion of the flow path is via bulk flow of fluid. In some embodiments, the valve comprises a deformer. In some embodiments, the deformer is elastic. In some embodiments, the deformer comprises a spring. In some embodiments, the deformer comprises an elastomeric membrane. In some embodiments, the deformer comprises bi-metallic composite configured to curl or flex along one or more axis in response to a stimuli. In some embodiments, the stimuli is heat. In some embodiments, a deformation of the deformer equals the configuration of the valve. In some embodiments, the deformer comprises a resting state. In some embodiments, the valve prevents flow of fluid through the first portion of the flow path. In some embodiments, the first portion of the flow path is defined by an elongated member. In some embodiments, the elongated member comprises a tube. In some embodiments, the elongated member comprises an open channel extending therethrough. In some embodiments, the elongated member comprises a cylindrical shape. In some embodiments, the atomizer comprises a heater configured to vaporize the fluid. In some embodiments, the atomizer comprises an ultrasonic energy generator configured to vaporize the fluid. In some embodiments, the heater is a resistive heater. In some embodiments, the heater is electronically coupled to the elongated member at a first end and to a chamber wall of the chamber at a second end. In some embodiments, the heater and the chamber wall are electrically insulated from one another. In some embodiments, the elongated member comprises one or more vent slots. In some embodiments, the one or more vent slots are configured to release the fluid. In some embodiments, the flow path comprises a diffusor configured to mix the vapor and the air. In some embodiments, the flow path comprises a baffle configured to release vapor into the chamber but retain an unvaporized portion of the fluid within the atomizer. In some embodiments, the atomizer comprises a baffle configured to release vapor into the chamber but retain an unvaporized portion of the fluid within the atomizer. In some embodiments, the baffle comprises one or more through-holes. In some embodiments, the through-holes are equal to or less than about 0.01 inches. In some embodiments, the through-holes are equal to or less than about 0.006 inches. In some embodiments, the flow path comprises a porous filter configured to release vapor into the chamber but retain an unvaporized portion of the fluid within the atomizer. In some embodiments, the atomizer comprises a porous filter configured to release vapor into the chamber but retain an unvaporized portion of the fluid within the atomizer. In some embodiments, the porous filter comprises one or more pores. In some embodiments, a substantial portion of the one or more pores are equal to or less than about 0.01 inches. In some embodiments, an average size of the one or more pores are equal to or less than about 0.01 inches. In some embodiments, a substantial portion of the one or more pores are equal to or less than about 0.006 inches. In some embodiments, an average size of the one or more pores are equal to or less than about 0.006 inches. In some embodiments, the vaporizer further comprises one or more processors configured to activate the atomizer in response to an inhalation of a user. In some embodiments, the vaporizer further comprises a fluid pump configured to actively pump the fluid through the flow path. In some embodiments, the vaporizer further comprises a venturi tube configured to create an amplified vacuum within a throat of the venturi tube in response to an inhalation of a user.

Provided herein is a hand-held vaporizer comprising: a reservoir configured to contain a fluid; an atomizer configured to form a vapor from the fluid; a flow path comprising a first portion originating in the reservoir and continuing to the atomizer and a second portion originating at an air inlet and joining the first portion after the atomizer to form a third portion of the flow path containing air from the air inlet and the vapor within a chamber of the atomizer; and a valve configured to modulate a flow of fluid through the first portion of the flow path wherein a configuration of the valve depends on a degree of vacuum applied to the chamber. In some embodiments, a primary means of fluid transportation through the first portion of the flow path is not via capillary action. In some embodiments, the primary means of fluid transportation through the first portion of the flow path is via bulk flow of fluid. In some embodiments, the valve comprises a deformer. In some embodiments, the deformer is elastic. In some embodiments, the deformer comprises a spring. In some embodiments, the deformer comprises an elastomeric membrane. In some embodiments, the deformer comprises bi-metallic composite configured to curl or flex along one or more axis in response to a stimuli. In some embodiments, the stimuli is heat. In some embodiments, a deformation of the deformer equals the configuration of the valve. In some embodiments, the deformer comprises a resting state. In some embodiments, the valve prevents flow of fluid through the first portion of the flow path. In some embodiments, the first portion of the flow path comprises an elongated member. In some embodiments, the elongated member comprises a tube. In some embodiments, the elongated member comprises an open channel extending therethrough. In some embodiments, the elongated member comprises a cylindrical shape. In some embodiments, the atomizer comprises a heater configured to vaporize the fluid. In some embodiments, the atomizer comprises an ultrasonic energy generator configured to vaporize the fluid. In some embodiments, the heater is a resistive heater. In some embodiments, the heater is electronically coupled to the elongated member at a first end and to a chamber wall of the chamber at a second end. In some embodiments, the heater and the chamber wall are electrically insulated from one another. In some embodiments, the elongated member comprises one or more vent slots. In some embodiments, the one or more vent slots are configured to release the fluid. In some embodiments, the flow path comprises a diffusor configured to mix the vapor and the air. In some embodiments, the flow path comprises a baffle configured to release vapor into the chamber but retain an unvaporized portion of the fluid within the atomizer. In some embodiments, the atomizer comprises a baffle configured to release vapor into the chamber but retain an unvaporized portion of the fluid within the atomizer. In some embodiments, the baffle comprises one or more through-holes. In some embodiments, the through-holes are equal to or less than about 0.01 inches. In some embodiments, the through-holes are equal to or less than about 0.006 inches. In some embodiments, the flow path comprises a porous filter configured to release vapor into the chamber but retain an unvaporized portion of the fluid within the atomizer. In some embodiments, the atomizer comprises a porous filter configured to release vapor into the chamber but retain an unvaporized portion of the fluid within the atomizer. In some embodiments, the porous filter comprises one or more pores. In some embodiments, a substantial portion of the one or more pores are equal to or less than about 0.01 inches. In some embodiments, an average size of the one or more pores are equal to or less than about 0.01 inches. In some embodiments, a substantial portion of the one or more pores are equal to or less than about 0.006 inches. In some embodiments, an average size of the one or more pores are equal to or less than about 0.006 inches. In some embodiments, the vaporizer further comprises one or more processors configured to activate the atomizer in response to an inhalation of a user. In some embodiments, the vaporizer further comprises a fluid pump configured to actively pump the fluid through the flow path. In some embodiments, the vaporizer further comprises a venturi tube configured to create an amplified vacuum within a throat of the venturi tube in response to an inhalation of a user.

The present disclosure provides for an electronic device including a processing unit for executing a plurality of operations; including, but not limited to a breath modulated flow control valve incorporated in a vaporizing device.

The electronic device may further include a storage unit (e.g., memory unit) for storing the plurality of operations, including an integrated vaporizer test product incorporating improved atomizer designs and breath modulated flow.

The present disclosure provides a breath-modulated valve incorporated in a wickless vaporizing device and a method of breath-modulated control of a wickless electronic vaporizing device.

In an embodiment, the present invention provides a breath-modulated valve incorporated in a wickless electronic vaporizing device. In one aspect, the breath-modulated valve can be elastomeric or bimetallic.

It is one object of the present invention to provide a method of breath-modulated control of electronic vaporizers, the method comprising providing a breath-modulated valve; optionally incorporating the valve in an electronic vaporizing device by connecting said valve to an opening in a reservoir and connecting an outlet to an improved atomizer.

In another aspect, the present invention provides an atomizer design including a vented/non-vented coil around stainless tubing and a breath-modulated valve incorporated in a wickless electronic vaporizer, where the atomizer can be an air-in-coil atomizer.

In another aspect, the present disclosure presents that utilizing a breath-modulated valve may allow improvements in the atomizer design to improve vaporization efficiency.

In an aspect, the present disclosure presents several improved atomizer designs of a vaporizer, wherein said design can be configured with a breath-modulated valve, optionally incorporated in a vaporizing apparatus, where said apparatus can be an electronic cigarette, where said valve is any of the valves, as described in this present disclosure.

In yet another aspect, the present disclosure presents an improved atomizer design of a vaporizer, wherein said design includes either a vented or non-vented coil around stainless tubing; wherein said improved atomizer can be configured, optionally with a breath-modulated valve, as described in this present disclosure, incorporated in a vaporizer; wherein said valve comprises any of elastomeric elements or bimetallic elements.

In yet another aspect, the present disclosure presents an improved atomizer design of a vaporizer, wherein said design can be an air-in-coil atomizer, wherein said atomizer can be configured, optionally with a breath-modulated valve incorporated in a vaporizing apparatus, where said apparatus can be an electronic cigarette, where said valve is any of the valves, as described in this present disclosure.

In yet another aspect, the present disclosure presents an improved atomizer design of a vaporizer, wherein said design can be an air-in-coil atomizer, wherein said atomizer can be configured, optionally, with a breath-modulated valve incorporated in a vaporizing apparatus, where said apparatus can be an electronic cigarette, where said valve is any of the valves, as described in this present disclosure.

In yet another aspect, the present disclosure presents an improved atomizer design of a vaporizer, wherein said design can be an air-over-coil atomizer, wherein atomizer can be configured, optionally with a breath-modulated valve incorporated in a vaporizing apparatus, where said apparatus can be an electronic cigarette, where said valve is any of the valves, as described in this present disclosure.

Still, in another aspect, the present disclosure presents an improved atomizer design of a vaporizer, wherein said design can be a porous filter atomizer, wherein said atomizer can be configured, optionally with a breath-modulated deformable valve incorporated, optionally, in a vaporizing apparatus, where said apparatus can be an electronic cigarette, where said valve is any of the valves, as described in this present disclosure.

Still, in another aspect, the present disclosure presents an improved atomizer design of a vaporizer, wherein said design can be a baffled filter atomizer, wherein said atomizer can be configured, optionally with a breath-modulated valve incorporated, optionally in a vaporizing apparatus, where said apparatus can be an electronic cigarette, where said valve is any of the valves, as described in this present disclosure.

In another aspect, the present disclosure presents an integrated vaporizing system incorporating various aspects of an improved atomizer designs and breath modulated flow, wherein an atomizer can be configured, optionally with a breath-modulated valve incorporated in a vaporizing apparatus, where said apparatus can be an electronic cigarette, where said valve is any of the valves, as described in this present disclosure; where said atomizer is any of the atomizers, as described in this present disclosure.

In yet another aspect, the present disclosure presents alternative enhancements in the heating elements for vaporization devices, illustratively, these are discussed in various aspects of the present disclosure, and can include, but may not be limited to, two heaters configured with a vented coil or non-vented coil around stainless tubing.

Provided in the present disclosure is a breath-modulated valve incorporated into a vaporizing device, like an electronic cigarette, where a wick is eliminated; said valve replaces a wick. In some instances, a method of breath-modulated flow control of a liquid vaporizer, the method comprising providing the liquid vaporizer, which is an electronic cigarette device, optionally, incorporating in said device a breath-modulated valve to replace a conventional wick, connecting the valve inlet to an opening in a reservoir, connecting the valve outlet to an improved atomizer; allowing flow from the reservoir into the atomizer, when a user inhales from a mouthpiece of the device, wherein the valve can be of elastomeric or bimetallic elements; wherein the atomizer can be any of the embodiments of atomizer design herein described.

The present disclosure may be drawn to a breath-modulated valve incorporated in a vaporizing device, when present, rendering said device wickless, where the said device is an electronic cigarette and a method of breath-modulated flow control for said device.

In one aspect, the present disclosure may be drawn to a breath-modulated valve incorporated in a vaporizing device, like an electronic cigarette; wherein the valve replaces a wick and said valve is made of elastomeric elements, where said elements are chosen from materials comprising rubbers, silicone (e.g., room temperature vulcanizing ("RTV") silicon), cured liquid silicone resin (e.g., NuSil MED-48xx series), or any other suitable elastomeric material.

In one aspect, the present disclosure may be drawn to a breath-modulated valve incorporated in a vaporizing device, like an electronic cigarette; wherein the valve, when present can replace a conventional wick, is made of bimetallic elements, where said elements are chosen, for example, from materials including steel and copper or steel and brass.

In yet another aspect, the present disclosure presents an improved configuration of an electronic vaporizer incorporated, optionally with a breath-modulated valve as a replacement of a wick in a conventional vaporizer, wherein said replacement can allow the incorporation of a normally closed elastomeric valve in a disposable reservoir, which opens only when the cartridge is mounted on the vaporizer, ready for use.

In yet another aspect, the present disclosure presents an improved configuration of an electronic vaporizer incorporated, optionally with a breath-modulated valve as a replacement of a wick in a conventional vaporizer, wherein said configuration allows for clean switching between different flavor liquids.

In yet another aspect, the present disclosure presents an improved configuration of an electronic vaporizer incorporated, optionally with a breath-modulated valve as a replacement of a wick in a conventional vaporizer, wherein said valve comprises any of elastomeric or bi-metallic elements.

In yet another aspect, the present disclosure presents an improved configuration of an electronic vaporizer incorporated, optionally with a breath-modulated valve as a replacement of a wick in a conventional vaporizer, wherein said valve comprises elastomeric or bi-metallic elements, wherein said elastomeric elements comprise rubbers, silicone (e.g., room temperature vulcanizing ("RTV") silicon), cured liquid silicone resin (e.g., NuSil MED-48xx series), or any other suitable elastomeric material.

In yet another aspect, the present disclosure presents an improved configuration of an electronic vaporizer incorporated, optionally with a breath-modulated valve as a replacement of a wick in a conventional vaporizer, wherein said valve comprises elastomeric or bi-metallic elements, wherein said bimetallic elements are any of composite materials where two different metals are bonded together; whereupon the difference in thermal expansion coefficient between the metals causes the composite material to curl or flex along one or more axis when heated. Heating energy may be provided by the heating element used in the vaporizer or by a separate heating element. The heating element may be triggered by a vacuum-sensitive or a manual switch in the device.

Also described herein are methods of vaporizing a material using a wickless hand-held vaporizer apparatus (including any of the apparatuses described above). For example, a method may include: sensing a user draw on a mouthpiece of the vaporizer apparatus; heating a heater to a vaporization temperature; controlling a flow modulator to flow a vaporizable fluid from a fluid reservoir of the vaporizer apparatus through a tube to the heater; vaporizing the vaporizable fluid to form a vapor; and emitting the vapor from the apparatus through the mouthpiece.

A method of vaporizing a material using a wickless hand-held vaporizer apparatus may include: sensing a user draw through a mouthpiece of the vaporizer apparatus; heating a heater to a vaporization temperature; controlling a flow modulator to flow a vaporizable fluid from a fluid reservoir of the vaporizer apparatus through a tube to the heater after the heater is at the vaporization temperature, wherein the flow is bulk flow through the tube; vaporizing the vaporizable fluid to form a vapor; emitting the vapor from the apparatus through the mouthpiece; and stopping flow through the tube by the flow modulator when the user is no longer drawing through the mouthpiece.

Also described herein are self-cleaning hand-held vaporizer apparatuses. For example, a self-cleaning apparatus may include: an elongate body having a mouthpiece; a reservoir configured to contain a vaporizable fluid; an atomizer within the elongate body configured to form a vapor from the vaporizable fluid, the atomizer comprising: a heater; a draw sensor configured to detect a user drawing on the mouthpiece; and a controller configured to control the heater and to initiate a self-cleaning cycle during a period when the user is not drawing on the mouthpiece so that the heater is heated to a self-cleaning temperature of greater than 400° C. for a self-cleaning period of greater than 1 minute.

Methods of self-cleaning using a hand-held vaporizer apparatus are also described. For example, a method of operating a self-cleaning vaporizer may include: determining when a user is not drawing through a mouthpiece of the vaporizer apparatus; heating a heater to a self-cleaning temperature that is greater than a vaporization temperature of the apparatus for a predetermined self-cleaning time that is greater than 2 minutes; and preventing flow of a vaporizable fluid from a fluid reservoir of the vaporizer apparatus through to the heater while the heater is at the self-cleaning temperature.

It shall be understood that different aspects of the invention can be appreciated individually, collectively, or in combination with each other. Various aspects of the invention described herein may be applied to any of the particular applications set forth below or for any other types of vaporizing device such as an electronic cigarette.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not restrictive.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIGS. 6A and 6B illustrate an open configuration (FIG. 6B) and closed configuration (FIG. 6B) of a vaporizer comprising a bi-metallic valve element, in accordance with embodiments.

FIGS. 8A and 8B illustrates a vaporizer comprising an atomizer comprising a heating element around an inlet tube, in accordance with embodiments. FIG. 8A shows a system diagram, and FIG. 8B shows a close-up of the inlet tube with vent holes.

in FIG. 8D, the reservoir is closed and/or may have a lower pressure, preventing fluid flow.

FIG. 10A shows a system diagram, and FIG. 10B shows a close-up of the diffusor.

DETAILED DESCRIPTION

Described herein are wickless vaporizing devices.

Vaporizing or vaporization may refer to a process in which heat or another aerosolization method (e.g., the application of ultrasonic energy) results in aerosol generation, or generation of fine droplets of fluid. Vaporization and/or atomization as used herein may occur with or without heating. The terms vaporization and atomization, vaporize and atomize, vaporizing and atomizing may be used interchangeably. A vaporizing device as used herein may be referred to as a vaporizer, electronic cigarette, e-cig, or device, and any of the aforementioned terms may be used interchangeably throughout. The vaporizing may generate vapor or aerosol from a fluid, e.g., for inhalation by a user.

In some instances, it may be beneficial for vaporizers to utilize a fluid flow modulator that enables modulation or control of fluid flow. Such a fluid flow modulator that enables control of fluid flow in a vaporizer may include a valve, as further described below. The configuration of the valve may depend at least partly on actions of a user (e.g., pressing a button, drawing a breath, etc.) and/or occur in response of one or more sensors on the vaporizer. The configuration of the valve may refer to a degree of openness of the valve. In some instances, the configuration of the valve may refer to the extent of fluid flow that is blocked and/or prevented by the valve. In some instances, the configuration of the valve may correspond to the position of the valve (e.g., translational, rotational) or valve elements.

In some instances, the valve may allow unhindered flow of fluid. In some instances, the valve may prevent fluid flow altogether. In some instances, the valve may be coupled to a flow path that allows allow bulk fluid flow. In some instances, the valve may be coupled to a flow path whose primary means of fluid transportation is via bulk fluid flow. In some instances, the valve may be coupled to a flow path that does not draw fluid via capillary action. In some instances, the valve may be coupled to a flow path whose primary means of fluid transportation is not via capillary action.

In some instances, it may be beneficial for vaporizers to utilize atomizers that are efficient and/or produce a high quality vapor. The ability to modulate or control flow of fluid through a flow path may enable use of such improved atomizer designs.

Figure 1:
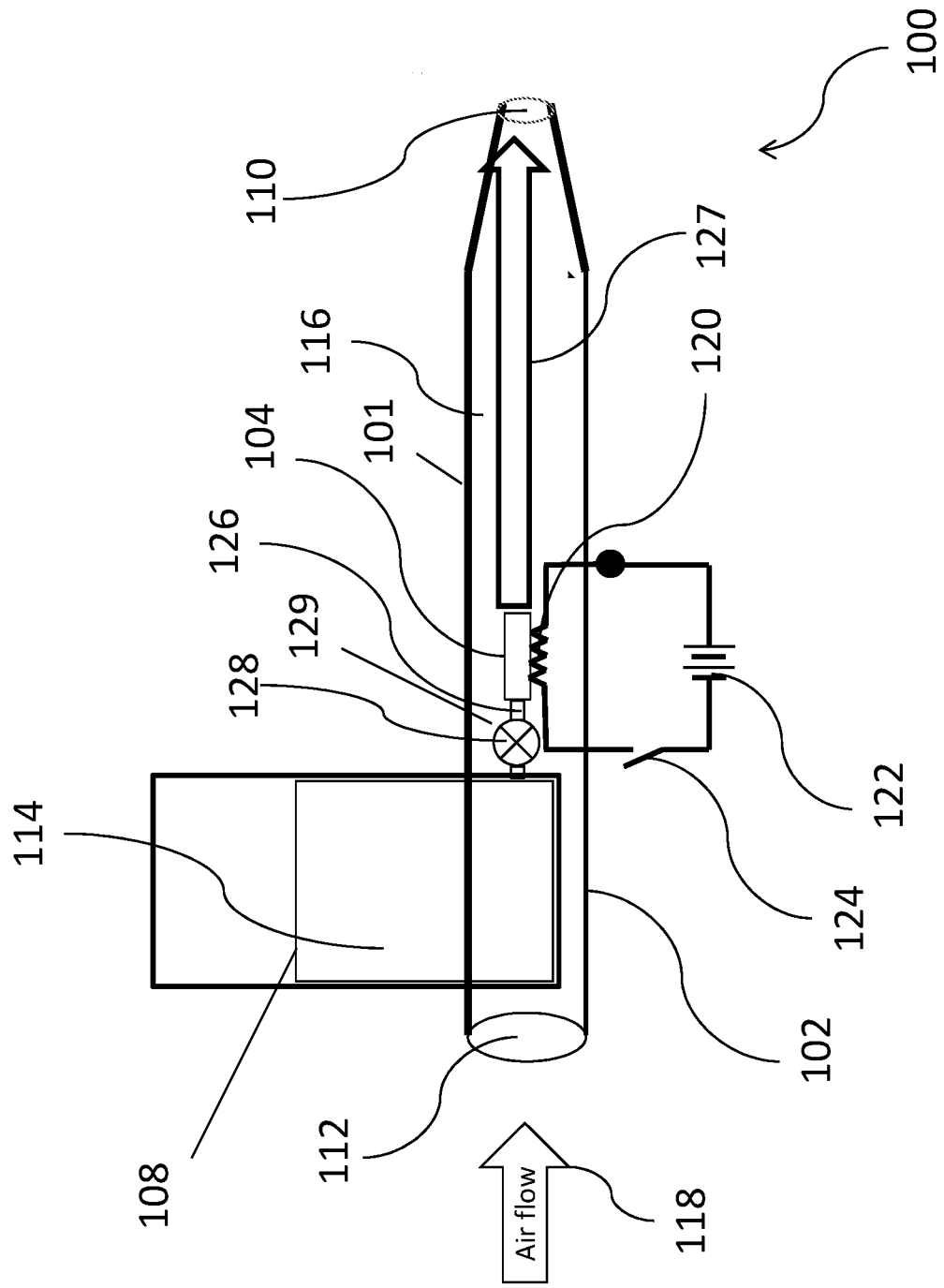
FIG. 1 illustrates a vaporizer with a fluid flow modulator, in accordance with embodiments.

FIG. 1 illustrates a vaporizer 100 with a fluid flow modulator 128, in accordance with embodiments. The vaporizer may comprise an elongate body 101, cartridge 102, an atomizer 104, and a battery unit 122. The elongate body 101, cartridge 102, atomizer 104, and battery unit 122 may be configured to be coupled to one another, e.g., removably or permanently. In some instances, the cartridge, atomizer, and/or battery unit may comprise three distinct units (e.g., components). In some instances, the elongate member 101, the cartridge 102, atomizer 104, and/or battery unit 122 may comprise a single integrated unit. For example, the cartridge 102 and atomizer 104 may include a single integrated component.

The elongate member 101 may include a proximal end 110 and a distal end 112. In some instances, the proximal end 110 of the vaporizer 100 may be configured to be placed in a user's mouth, e.g., may include a mouthpiece. In some instances, the distal end 112 of the elongate member may be configured to be coupled to a battery unit and/or may allow inflow of air (e.g., airflow into the device).

The vaporizer 100 may include one or more flow paths. In some instances, the flow path may include a directionality. A flow path as used herein may refer to any path through which liquid, vapor, and/or air may flow. In some instances, the flow path may be defined by an elongated member, tube, channel, or a chamber through which liquid, vapor, and/or air may flow. In some instances, the flow path may refer to a flow of liquid, vapor, and/or air starting from a reservoir described further below. In some instances, the flow path may refer to a flow of liquid, vapor, and/or air through a mouthpiece of the vaporizer. For example, the flow path may refer to a flow path from a reservoir to an atomizer to a mouthpiece of the vaporizer. For example, the flow path may refer to a flow path from anywhere to a mouthpiece of the vaporizer. The flow path may comprise one or more portions. For example, a flow path may comprise one, two, three, four, five, six, seven, eight or more portions.

For example, a flow path may comprise fluid flow path 126 from a fluid reservoir 108 to the atomizer 104 (e.g., for fluid flow) and a vapor path 127 to deliver vapor from the atomizer to a proximal end 110 or outlet (e.g., mouthpiece) of the vaporizer 100. The flow path can further include an air flow path 118 comprising airflow coming from outside of the vaporizer 118 and into an inner chamber 116 of the vaporizer 101. The fluid flow path 126 (i.e., for flow of liquid) from the reservoir 108 to the atomizer 104 may herein be referred to as a first portion of a flow path, or a first flow path. The vapor flow path 127 (e.g., for vapor) from the atomizer 104 to the outlet 110 (e.g., mouthpiece) of the vaporizer 100 may herein be referred to as a second portion of a flow path, or a second flow path. The air flow path 118 (i.e., of air) from outside of the vaporizer 100 to an inner chamber 116 of the vaporizer 100 may herein be referred to as a third portion of a flow path, or a third flow path.

In some instances, the elongate member 101 may include one, two, three, four, five, six, or more openings. For example, the elongate member 101 may include openings on each of the proximal end 110 and the distal end 112. In some instances the openings on each of the proximal end and the distal end may define a beginning and end of a chamber or channel through which air may flow. In some instances, the one or more openings may be located elsewhere on the elongate member 101, e.g., on a mid-section or on a side of the elongate member 101.

The cartridge 102 can include a fluid reservoir 108. A cartridge as used herein may refer to a body of the electronic cigarette that comprises a reservoir. The 102 cartridge may be made of any material such as plastic or metal. In some instances, the cartridge 102 may comprise a plurality of materials, e.g., elastomers, metals, and polymers. In some instances, the cartridge 102 may comprise a container, e.g., a small disposable container.

The reservoir 108 may be configured to contain a carrier fluid ("fluid") for the vaporizable fluid 114, e.g., a propylene glycol (PG) and/or vegetable glycerin (VG) based liquid solution. In some instances, the fluid may comprise nicotine and/or a flavoring. In some instances, the reservoir may be configured to contain thick liquids, non-liquids, and/or waxes. In some instances, the reservoir may be configured to contain organic materials and/or organic material formulations. Organic materials may comprise vaporizable (aerosolizable) materials that are any of a thick liquid, non-liquid and/or waxes selected from any of cannabis, cannabis extracts, and a mixture therefrom, which include extracts currently known in art. Organic material formulations may comprise vaporizable (aerosolizable) formulations that are any of a thick liquid, non-liquid and/or waxes, where said formulations comprise as main ingredient an extract selected from any of cannabis, cannabis extracts, and a mixture therefrom, which include the extracts currently known in art. Exemplary formulations of liquid are described in U.S. patent application Ser. No. 14/271,071, filed May 6, 2014, titled "NICOTINE SALT FORMULATIONS FOR AEROSOL DEVICES AND METHODS THEREOF," now U.S. Patent Application Publication No. 2014-0345631-A1, the entirety of which is incorporated by reference herein.

The cartridge 102 may be configured to be coupled to the atomizer 104. In some instances, the cartridge 102 may house the atomizer 104, and the atomizer 104 may be a part of the cartridge. A cartridge 102 that houses an atomizer 104 or is integrated with the atomizer as a single unit may herein be referred to as a cartomizer. In some instances, the atomizer 104 may be housed within a chamber 116 of the elongate body 101. In some instances, the chamber 116 may be defined by a channel through which air may travel, e.g., from the distal end to the proximal end. In some instances, the atomizer 104 may be housed within the chamber 104 and be in communication with open air from flow path 118 that may flow through the vaporizer 100.

The atomizer 104 can include a heating element 120. In some instances, an atomizer may refer to a component configured to form vapor from a fluid, e.g., using a heating element. The atomizer 104 can include and/or be coupled with an inner elongated member 129 housing the fluid flow path 126 (i.e., the inner elongated member 129 defines the first flow path). The atomizer 104 may be configured to generate heat via the heating element 120. For example, the heating element 120 may include a wire or a coil, e.g., a small length of resistance-wire or a resistive coil. While heating elements comprising wire and/or coils are primarily discussed herein, it is to be understood that any heating element may be used in place of the wire and/or coils.

In some instances, the heating element 120 may be within or be a part of the flow path, further described below.

The heating element 120 may be operably coupled to the battery unit 122 (e.g., via a switch 124). When the switch 124 is activated, current may flow through the heating element 120 and generate heat. The switch 124 may be activated by one or more methods, e.g., a user pushing a button, a user inhaling from the mouthpiece, based on sensors, etc. For example, a user may inhale from a vaporizer and a pressure sensor may detect the inhalation and activate the switch such that the heating element heats up. In some instances, the vaporizer may comprise one or more processors configured to activate the switch 124 in response to a response of the sensors. In some instances, the one or more processors may serve to modulate power applied to the heating element 120, measure the resistance of the heating element 120, and indirectly determine its temperature, sense inputs from the user (button, motion, capacitive, or other) to change the operating state or parameters of the device. Exemplary methods of activating and/or controlling the heater are further described in U.S. patent application Ser. No. 15/053,927, filed Dec. 23, 2014, titled "VAPORIZATION DEVICE SYSTEMS AND METHODS," now U.S. Patent Application Publication No. 2016-0174611-A1, the entirety of which is incorporated by reference herein.

The battery unit 122 may comprise a battery and/or battery housing. The battery may be a rechargeable battery, e.g., rechargeable lithium-ion battery. In some instances, the battery unit may comprise electronic components (e.g., circuity, processors, LED lights, etc.) required for operation of the vaporizer 100. Alternatively or in addition, electronic components may be housed elsewhere on the vaporizing device 100, e.g., on the cartridge 102 or on a separate component. In some instances, the battery and/or electronic components may be housed within the battery housing. In some instances, the battery unit may comprise one or more indicators. An indicator (e.g., visual, auditory, etc.) such as an LED may indicate activation (e.g., use) and/or inactivation of the vaporizer. For example, a colored LED may be included in the battery unit and may respond to inhalation of a user.

In some instances, the battery unit 122 may comprise one or more sensors, e.g., airflow, pressure sensor, vibration sensor, accelerometer, etc. The one or more sensors may sense usage of the vaporizer 100 by a user. For example, a pressure sensor and/or an airflow sensor may sense a user drawing a breath (e.g., inhale) through the vaporizer. For example, an accelerometer may sense a movement of the vaporizer. In some instances, a switch may activate (e.g., with aid of a processor) based on the sensed inhalation of a user and the heating unit may generate heat, as previously described herein. In some instances, the vaporizer may activate or deactivate based on an output of the one or more sensors (e.g., accelerometer).

The atomizer 104 may comprise a specific resistance measured in ohms. The resistance of the atomizer 104 and/or a given voltage of the battery may comprise parameters affecting an amount of vapor produced by a vaporizing device. For example, a high resistance and/or a low voltage used for a vaporizing device may result in less vapor (e.g., aerosol) production. For example, a low resistance and/or a high voltage used for a vaporizing device may result in more (e.g., thicker) vapor production and a stronger throat hit. In some instances, a low resistance and/or a high voltage for a given voltage may result in a burnt taste of the aerosol. In some instances, a low resistance and/or a high voltage for a given voltage may result in a pronounced flavor of the aerosol. In some instances, the vaporizer 100 can include a variable voltage. Variable voltage vaporizers may allow a user to select an operating voltage of the device's battery. Being allowed to select an operating voltage of the device's battery may allow the vaporizing device to produce a consistent vapor volume regardless of the remaining power.

The atomizer 104 may comprise one, two, three, four, five or more heating elements 120. An atomizer comprising more heating elements may be able to generate more vapor than an atomizer comprising less heating elements. An atomizer comprising more heating elements may require more battery power than an atomizer comprising less heating elements. For example, the atomizer 104 may include two coils. The two coils may each be of the same resistance. The two coils may be wired in parallel and a total resistance may be half the resistance of either coil. In some instances, a dual coil vaporizer may produce double the vapor than a single coil vaporizer. In some instances, a dual coil vaporizer may require more battery power than a single coil vaporizer.

In some instances, the atomizer 104 may be positioned between the cartridge 102 and the battery unit 122. For example, the atomizer 104 may be positioned at a center of the cartridge and the battery. Alternatively, a relative position of the atomizer 104 may be anywhere relative to the cartridge and/or the battery (e.g., proximal to the battery and/or cartridge, located at a far end of the cartridge, etc.).

Fluid 114 from the reservoir 108 may be delivered to a vicinity of heating element 120 through the inner elongated member 129, e.g., a tube, for vaporization. Vicinity as used herein may refer to a distance close enough such that fluid may be vaporized by the heating element 120. In some instances, the inner elongated member 129 may define the first flow path 126. The first flow path 126 may be a first portion of a flow path extending from the fluid reservoir 108 to outlet at the proximal end 110 of the elongate body 101. Fluid from the reservoir 108 may be operably coupled to the heating element 120 through the first flow path 126 or the elongated member 129. The inner elongated member 129 may be coupled to the heating element 120 and/or the reservoir 108, e.g., removably or permanently. In some instances, the inner elongated member 129 and/or the first flow path may physically extend from the reservoir 108 to a vicinity of the heating element 120.

In some instances, the inner elongated member 129 can include a material such as stainless steel that can act as a resistive heater. For example, the inner elongated member 129 may be coated and/or plated with a resistive material. For example, the inner elongated member 129 may be coated and/or plated with a thin nickel plating.

The heating element 120 may be coupled to the inner elongated member 129 (e.g., a distal end of the elongated member). For example, the heating element 120 may be a resistive coil that surrounds or is wound around a distal end of the inner elongated member 129. In some instances, the heating element 120 may be coupled to the inner elongated member 129 with aid of one or more intermediaries. For example, the heating element 120 may be held in a vicinity of the inner elongated member 129 via intermediaries. For example, the heating element 120 may be coupled to an intermediary housing or an intermediary tube which may be configured to receive or surround the inner elongated member 129. In some instances, the intermediary housing (e.g., intermediary tube) and the inner elongated member 129 may comprise complimentary mating features such that the heating element 120 and the inner elongated member 129 may be coupled together. The heating element 120, alone or together with any intermediaries may also be referred to herein as a heater. In some instances, the heater may comprise a heating element 120 and no intermediaries. For example, the heater may be directly coupled to the inner elongated member 129. In some instances, the heater may include a heating element 120 and the aforementioned intermediaries.

The heating element 120 may directly contact the inner elongated member 129. In some instances, the heating element 120 may be in a vicinity of the inner elongated member 129 but may be physically separated from the inner elongated member 129. In some instances, portions of the heating element 120 may directly contact the inner elongated member 129 while other portions are physically separated from the inner elongated member 129. The heating element 120 may vaporize liquid delivered through the inner elongated member 129 and generate aerosol (e.g., vapor). The generated aerosol may be delivered to a user through the distal end 110 of the vaporizer elongated member 101, e.g., through a mouthpiece.

Although "wickless" variations are described herein, the vaporizers described herein may include a wick in addition to any of the other features (e.g., self-cleaning heaters, valves, pressure control of the vaporizable material, diffusers, baffles, etc.). For example, in some instances, the inner elongated member 129 may include a wicking element or a wick. The wicking element may draw fluid via capillary action. The wicking element may wick, transport, or draw liquid from the reservoir 108 onto a vicinity of the heating element 120 of the vaporizer 104, which may vaporize the liquid. The wicking element may include silica, cotton, or any other appropriate material configured to transport fluid via capillary action. For example, the wicking element may comprise a stainless steel mesh wick. In some instances, one portion of the wicking element may be submerged in liquid 114 within the reservoir 108 (e.g., through an orifice in the reservoir). A non-submerged portion of the wicking element may be positioned near or may contact the heating element 120 of the atomizer 104. Liquid may travel through the wicking element via capillary action, e.g., from the submerged portion into the non-submerged portion of the wicking element. In some instances, a flow of liquid through the wicking element is not be modulated or be blocked (e.g., prevented). In some instances, a flow of liquid through the wicking element is not be controlled. In some instances, the wick may provide a direct, uninterrupted open path between inside of the reservoir 108 and outside of the reservoir 108.

Alternatively or in addition, the inner elongated member 129 may include a hollow passage, opening, or channel. Thus, the inner elongated member 129 may comprise a distal end, a proximal end, and an open channel extending from the distal end to the proximal end. In some instances, the open channel may be blocked, e.g., by the flow modulator 128.

Thus, described herein are wickless vaporizers, in which vaporizable material is moved from a fluid reservoir to an atomizer (e.g., heater) without a wick or without using capillary action. Such wickless variations may be beneficial because they may allow enhanced control of the dose (e.g., amount of vaporizable material delivered to the atomizer/heater and therefore the amount of vapor formed). In general, any of the apparatuses described herein may include a fluid flow modulator for controlling the flow (e.g., bulk or mass-transport flow) of vaporizable fluid from the reservoir to the atomizer/heater. The fluid flow modulator may include multiple components, including a valve and/or a pressure regulator. In some variations the fluid flow modulator may not include a valve; for example, the apparatus may be configured so that vaporizable liquid is retained by surface tension. When one or more pressure-regulating elements ("pressure regulator") is included as part of the fluid flow modulator, the pressure-regulating elements may include a venturi (as will be described in greater detail herein), or an active pumping/compressing element (e.g., for pumping air and/or vaporizable fluid into the reservoir). In some variation a pressure-regulating element may be configured to reduce or expand the volume of the fluid reservoir to increase or decrease the pressure therein. In some variations a pressure-regulator includes a valve for opening/closing the reservoir to ambient pressure (see, e.g., FIGS. 8C and 8D, described below).

In some instances, the inner elongated member 129 may be a tube, also referred to herein as an inlet tube. The tube may be of any shape, e.g., cylindrical, rectangular, cuboid, etc. The tube may comprise an open channel extending from the reservoir to a vicinity of the heating element or an atomizer. The tube may be made of any material including metals and polymers. For example, the tube may comprise stainless steel, titanium, copper, silver gold, etc. In some instances, the tube may be a hypotube. In some instances, the tube may comprise a heating element. For example, a tube may comprise a resistive heater. For example, the tube may comprise a material such as stainless steel which may act as a resistive heater. For example, the tube may be coated and/or plated with a resistive material. For example, the tube may be coated and/or plated with a thin nickel plating.

The inner elongated member 129 tube may allow natural flow (e.g., bulk flow, mass flow) of fluid from the reservoir 108 onto a vicinity of the heating element 120 for vaporization of the liquid. In some instances, a flow of fluid from the reservoir 108 onto a vicinity of the heating element 120 may be aided by other forces, e.g., vacuum created from an inhalation of a user, an external force (e.g., force from a cocked spring, active fluid pump), and/or gravity. For example, the inner elongated member 129 tube may be coupled to an active fluid pumping element, e.g., micropump. In some instances, the inner elongated member 129 tube may include an active fluid pumping element to aid flow of fluid (e.g., mass flow of fluid). For example, the reservoir 108 can be flexible, and a spring may be installed in compression outside the reservoir 108 and inside an outer rigid housing. Alternatively or additionally, the reservoir 108 can be a rigid-walled chamber where one wall comprises a moveable piston (such as in a syringe) and a compression spring may be installed in compression on the other side of the piston.

In some instances, a flow of liquid through the inner elongated member 129 tube may be modulated or be blocked, e.g., with the fluid flow modulator 128. A fluid flow modulator may refer to any device, component, mechanism or configuration that modulates a flow of fluid. While the fluid flow modulator is shown located within the inner elongated member 129 (and in the first flow path 126), it is to be understood that the fluid flow modulator 128 may be located anywhere, e.g., in the cartridge 102, on the battery unit 122, etc. The fluid flow modulator 128 may act as a valve that controls passage of fluid. Any of the fluid flow modulators described herein may include a valve. A fluid flow modulator may act as a valve that controls or modulates passage of fluid within or through one or more flow paths, e.g., the first flow path. The fluid flow modulator 128 may modulate and/or control fluid flow through the inner elongated member 129. The fluid flow modulator 128 may thus modulate fluid flow from the reservoir 108 to a vicinity of the atomizer 104 or the heating element 120, e.g., through the first flow path 126. The fluid flow modulator 128 may prevent fluid flow and/or allow unhindered fluid flow.

Figure 13:
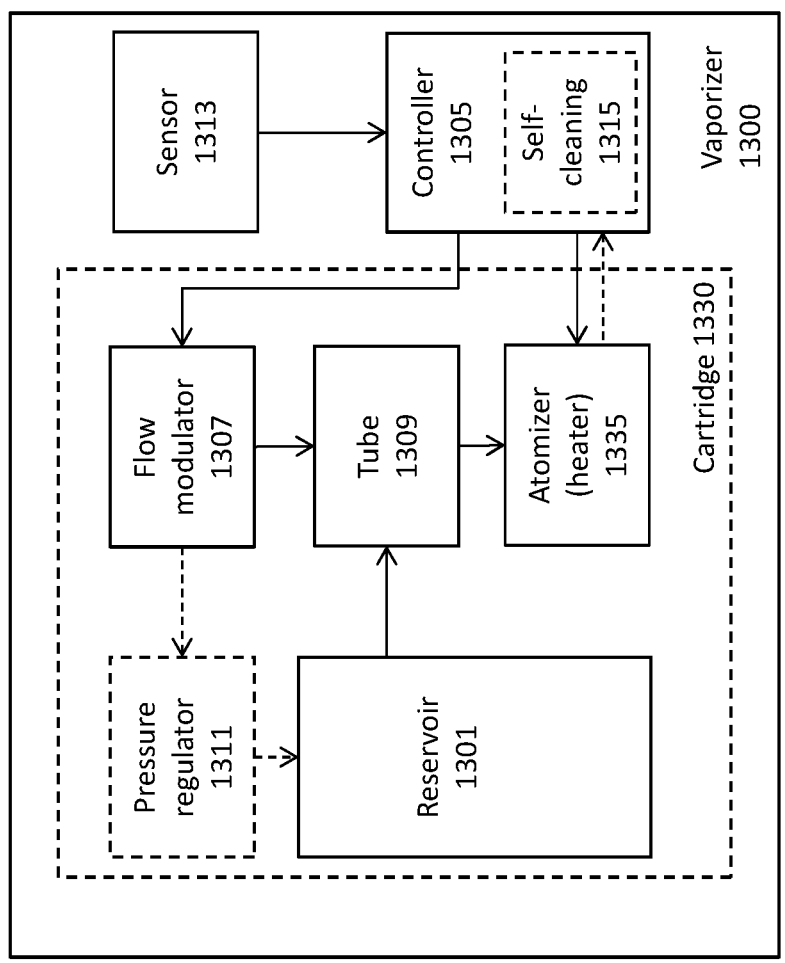
FIG. 13 schematically illustrates one example of a vaporizer apparatus as described herein.

In any of the variations described herein, the apparatus may include a controller controlling the heat of the atomizer/heater (e.g., the resistance through the coil), and/or the fluid flow modulator. One or more sensors (touch sensors, lip sensors, draw sensors, etc.) may provide input to the controller, and this input may be used to operate fluid flow modulator; for example, flow from the reservoir may be provided only when the heater is determined or estimated to be at a predetermined (vaporization) temperature (e.g., between 100 and 400° C., etc.). A separate controller for controlling the fluid flow modulator may be provided or the same controller used to control the heater may be used. The heater may be regulated using a control loop, e.g., based on the resistance of the heating element. The heater temperature may be raised when a draw is detected (e.g., by capacitive lip sensing, etc.), and vaporizable fluid may be flowed to the heater when the heater temperature is within a predetermined range. FIG. 13 schematically illustrates an example of a vaporizer apparatus 1300 as described herein. In this example, a controller 1305 controls the atomizer (heater 1335), and may receive input from one or more sensors (including a resistance/voltage input from the heater, shown in dashed line, capacitive/touch/lip sensors, accelerometers, etc.). The controller may control the flow modulator 1307, such as a valve or valves connected to the tube 1309 through which vaporizable fluid flows from the reservoir 1301 to the atomizer 1335 and/or a pressure regulator 1311 that may be optionally connected to the reservoir and/or optionally controlled by the controller 1305. Any portion of the vaporizer 1300 may be part of a removable and/or disposable cartridge 1330, e.g., the reservoir, and/or tube, flow modulator 1307 and atomizer 1335.

Returning to the example shown in FIG. 1, in some embodiments, the fluid flow modulator 128 can include a deformable element, also referred to herein as a deformer, such as a spring, elastomeric element, bimetallic elements, and the like further described elsewhere. The deformer can be elastic, e.g., may resume a resting state spontaneously after contraction, dilation, and/or distortion. The deformer can present a bias force. The bias force can maintain the fluid flow modulator 128 (e.g., valve) in a default configuration (e.g., equilibrium, resting state, steady state configuration, etc.). In some instances, the bias force can maintain the fluid flow modulator 128 in a closed configuration. The closed configuration may correspond to a resting state of the fluid flow modulator 128, e.g., not under external forces. The closed configuration may correspond to an equilibrium state of the deformer.

The fluid flow modulator 128 can include an open configuration and a closed configuration. The open configuration can allow unhindered fluid flow, and the closed configuration may allow no fluid flow, e.g., within the first flow path 126. In some instances, the fluid flow modulator 128 can comprise a plurality of discrete configurations with each configuration allowing a distinct level of fluid flow or corresponding to a discrete level of a hindered fluid flow, e.g., within the first flow path 126. In some instances, the fluid flow modulator 128 may include a continuum of configurations allowing any level of fluid flow between unhindered fluid flow and no fluid flow, e.g., within the first flow path. The fluid flow modulator 128 may include a resting state and an active state. A resting state may refer to a state of the fluid flow modulator when no external forces act upon the fluid flow modulator. An active state may refer to a state of the fluid flow modulator when external forces act upon the fluid flow modulator. In some instances, the resting state may correspond to the closed configuration. In some instances, the active state may correspond to the open configuration. In some instances, the active state may correspond to a configuration in-between the open configuration and the closed configuration.

The configuration or state of the fluid flow modulator 128 may be based on, or depend upon, a pressure of inhalation from a user. The configuration of the fluid flow modulator 128 may refer to a degree of openness of the valve. In some instances, the configuration of the fluid flow modulator may refer to an extent of fluid flow that is blocked and/or prevented by the fluid flow modulator. In some instances, the configuration of the fluid flow modulator may correspond to a position of the fluid flow modulator (e.g., translational, rotational) or valve elements. The configuration of the fluid flow modulator may include an open configuration, a closed configuration, and any configuration in between. Thus, in some instances, a user may draw (e.g., inhale) on a mouthpiece of the vaporizer 100, and the inhalation may create a vacuum or negative pressure within the vaporizer 100. For example, the inhalation of the user may create a vacuum or negative pressure within chamber 116, inner elongated member 129, and/or fluid flow modulator 128. The configuration or state of the fluid flow modulator 128 may be affected by the strength of vacuum or negative pressure created from an inhalation from a user.

Further, the degree (e.g., strength) of an inhalation may correspond to a configuration of the fluid flow modulator 128. In some instances, the degree of vacuum created within chamber 116 may correspond to a configuration of the fluid flow modulator 128. The degree (e.g., strength) of inhalation may correspond to the degree of openness of the fluid flow modulator. In some instances, the degree of vacuum created within chamber 116 may correspond to the degree of openness of the fluid flow modulator 128.

For example, the fluid flow modulator 128 may be put in an open configuration for inhalation of the user that creates a vacuum (e.g., negative pressure) above a certain threshold. The fluid flow modulator 128 may likewise be put in (e.g., remain in) a closed configuration for inhalation of the user that creates a vacuum (e.g., negative pressure) below a certain threshold. Further, the modulator may be put in a configuration between the open configuration and a closed configuration for an inhalation of a user that is in between the two thresholds. In some embodiments, the degree (e.g., strength) of inhalation may correspond to the degree of fluid flow, e.g., from the reservoir 108 to the vicinity of the heating element 120.

Alternatively or in addition, the configuration or state of the fluid flow modulator 128 may be based on, or depend upon, the output of one or more sensors. As previously described herein, the vaporizer 100 may include one or more sensors. For example, the vaporizer 100 may comprise a pressure sensor, an air flow sensor, accelerometer, and the like. The one or more sensors may affect a configuration of the fluid flow modulator 128, e.g. directly or indirectly. For example, in response to the output of the one or more sensors, the fluid flow modulator 128 may become more or less responsive (e.g., sensitive) to inhalation of the user. For example, the user may draw (e.g., inhale) on a mouthpiece of the vaporizer 100, and the sensor may sense the pressure that is exerted by the inhalation and output a response (e.g., binary or a continuum). The configuration of the fluid flow modulator 128 (e.g., open, closed, or in between) may correspond to the output of the sensor.

Alternatively or additionally, the configuration or state of the fluid flow modulator 128 may be based on, or depend upon, an external (e.g., environmental) stimuli. For example, the fluid flow modulator 128 may be configured to sense an external stimuli and respond. For example, the fluid flow modulator may respond to an increase or decrease in temperature (e.g., change configurations based on the increase or decrease). As another example, the fluid flow modulator 128 may respond to an electrical simulation (e.g., change configurations based on the electrical stimulation). As another example, the fluid flow modulator 128 may respond to an increase or decrease in pressure (e.g., change configurations based on the increase or decrease in pressure). In some embodiments, the fluid flow modulator 128 may change configurations in response to inhalation by the user (e.g., the inhalation can activate the atomizer (e.g., heating element), resulting in an increase in temperature that can be is sensed by the fluid flow modulator 128).

Fluid from the reservoir 108 may flow through the inner elongated member 129 and/or within the first flow path 126 at a liquid flow rate. In some instances, the liquid flow rate may be equal to or greater than about 0, 20, 40, 60, 80, 100, 120, 140, 160, 180, 200, 220, 240, 260, 280, or 300 microliters/min. In some instances, the liquid flow rate may be equal to or less than about 0, 20, 40, 60, 80, 100, 120, 140, 160, 180, 200, 220, 240, 260, 280, or 300 microliters/min. In some instances, the liquid flow rate may range from about 20 to 200, 40 to 180, or 60 to 160 microliters/min. For example, the liquid flow rate may vary depending on the other forces (e.g., inhalation of a user, an external force (e.g., that from a cocked spring) and/or gravity).

The liquid flow rate may depend on a configuration of the fluid flow modulator 128. In some instances, the liquid flow rate may be equal to or greater than about 0, 20, 40, 60, 80, 100, 120, 140, 160, 180, 200, 220, 240, 260, 280, or 300 micro liters/min in an open configuration (e.g., of the valve). In some instances, the liquid flow rate may be equal to or lesser than about 0, 20, 40, 60, 80, 100, 120, 140, 160, 180, 200, 220, 240, 260, 280, or 300 micro liters/min in an open configuration (e.g., of the valve). In some instances, the liquid flow rate may be equal to or greater than about 0, 20, 40, 60, 80, 100, 120, 140, 160, 180, 200, 220, 240, 260, 280, or 300 micro liters/min in a closed configuration (e.g., of the valve). In some instances, the liquid flow rate may be equal to or lesser than about 0, 20, 40, 60, 80, 100, 120, 140, 160, 180, 200, 220, 240, 260, 280, or 300 micro liters/min in a closed configuration (e.g., of the valve).

In some instances, the liquid flow rate may be controllable, e.g., via the fluid flow modulator 128. For example, the liquid flow rate may be controllable within a range of about 0 to 100, 0 to 120, 0 to 140, 0 to 160, 0 to 180, 0 to 200 or 0 to 300 microliters/min.

In some instances, the vaporizing device 100 may further comprise an absorbent material (e.g., sponge) therein. For example, the cartridge 102 may comprise an absorbent material, and the absorbent material may be housed within the cartridge 102. The absorbent material may rest on a barrier (e.g., plastic barrier) which separates the absorbent material from an opening (e.g., on the mouthpiece). The absorbent material may block passage of the liquid. For example, the absorbent material may prevent liquid from flowing through the cartridge 102 into a user's mouth.

In some instances, the vaporizing device 100 may include a venturi tube. The venturi tube may include an open channel. The venturi tube may comprise one, two, three, four, five or more openings. For example, the venturi tube may comprise an inlet opening configured for inflow of air (e.g., influx of air) and an outlet opening configured for outflow of air. In some instances, the venturi tube may comprise a narrowing, e.g., at a mid-section. The narrowing of the venturi tube may herein be referred to as a throat of the venturi tube. In some instances, the throat of the venturi tube may be located substantially at a mid-section of the venturi tube. Alternatively, a narrowing may be located elsewhere, e.g., further below near an outlet of the venturi tube. In some instances, the venturi tube may comprise an opening (e.g., at a midsection, at the throat) configured to be coupled to a separate tube. The separate tube may comprise a separate open channel. The separate tube may be configured for airflow or creation of a vacuum. The separate tube or the throat may be configured to be coupled to a separate element (e.g., valve, air channel, etc.), as further described below.

In some instances, the venturi tube may comprise an inlet with a first diameter. The venturi tube may gradually narrow and become narrowest at a mid-section comprising a second diameter. The venturi tube may thereafter gradually widen to an outlet with a third diameter. The mid-section may be coupled to a separate tube. In some instances, the first and third diameter may be the same. In some instances, the first, second, and third diameter may be the same. In some instances, the first, second, and third diameters may be different. In some instances, two of the first, second, and third diameters may be the same.

The ratio of the first diameter to the second diameter may be equal to or less than about 0.25:1, 0.5:1, 1:1, 2:1, 3:1, 4:1, 5:1, 6:1, 7:1, or 8:1. In some instances, the ratio of the first diameter to the second diameter may be equal to or greater than about 0.25:1, 0.5:1, 1:1, 2:1, 3:1, 4:1, 5:1, 6:1, 7:1, or 8:1. In some instances, the ratio of the first diameter to the second diameter may be in between about 0.25:1, 0.5:1, 1:1, 2:1, 3:1, 4:1, 5:1, 6:1, 7:1, or 8:1.

In some instances, the venturi tube may be configured to modulate and/or control the configuration of the fluid flow modulator 128 (e.g., by creating the pressure differential). The venturi tube may be configured to create a pressure differential across the flow modulator 128. The venturi tube may be configured to amplify a pressure differential across the flow modulator 128. In some instances, the venturi tube may be configured to create a pressure differential across a flow modulator in response to an inhalation by a user and thus transform the configuration of the fluid flow modulator 128 (e.g., from a closed to an open configuration). In some instances, the venturi tube (e.g., together with the cartridge 102 or chamber 116) may be configured to create an amplified vacuum with the separate tube and/or the throat.

The vaporizer 100 may comprise a single integrated device or a plurality of discrete components. One or more components of the vaporizer 100 may be reusable. One or more components of the vaporizer 100 may be disposable. For example, if liquid in the cartridge 102 is depleted, the liquid reservoir may be refillable. In some instances, if liquid in the cartridge 102 is depleted, the cartridge 102 may be configured to be disposed and replaced with another pre-filled cartridge. In some instances, the cartridge 102 may be configured to be replaced after the atomizer 104 has been used (e.g., after a predetermined number of uses or a predetermined period of time).

Figure 2:
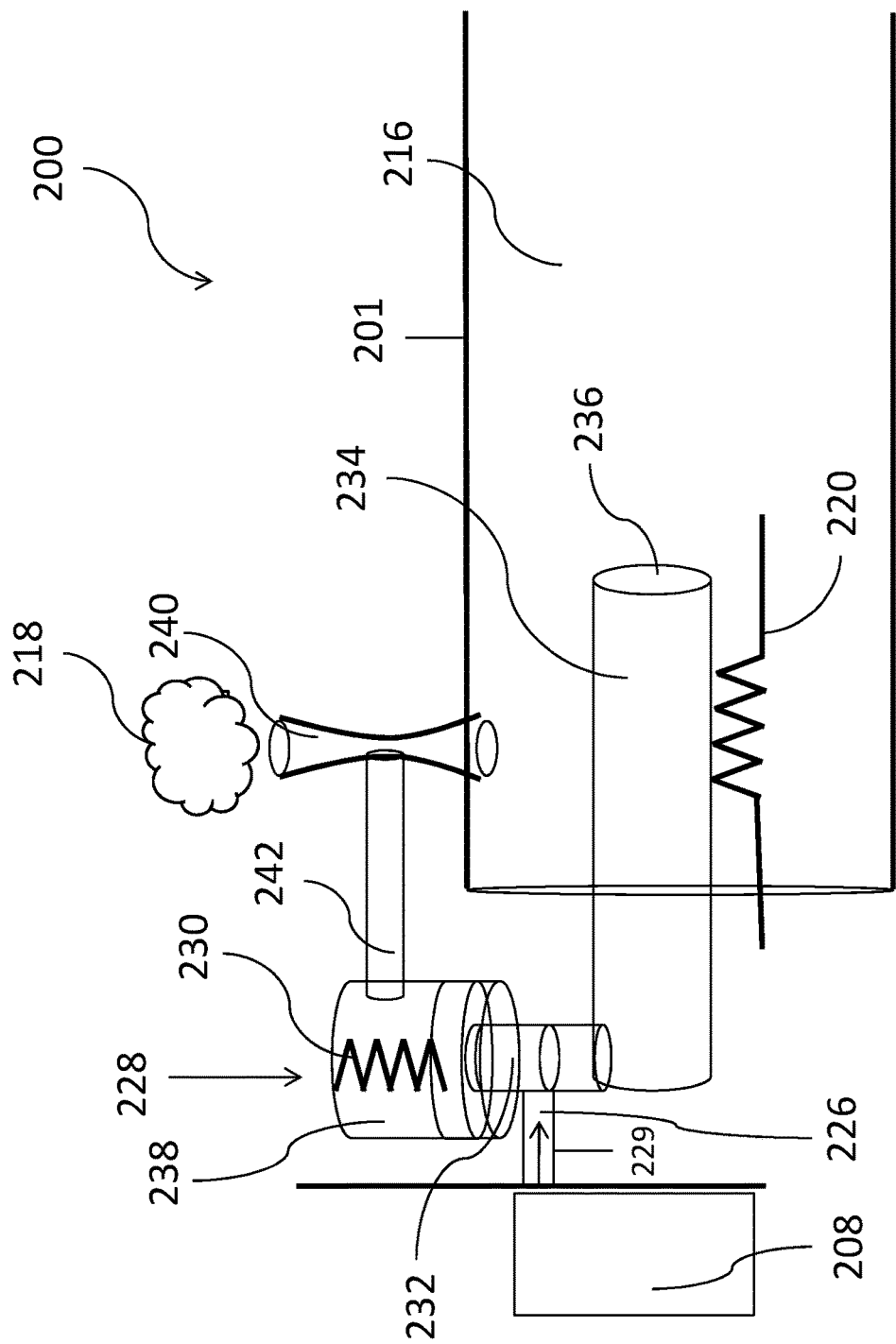
FIG. 2 illustrates a closed configuration of a vaporizing device utilizing a spring, in accordance with embodiments.

FIG. 2 illustrates a closed configuration of an exemplary vaporizing device 200 including similar features to vaporizing device 100. Vaporizer device 200, however, includes a flow modulator 228 comprising a spring 230 and fluid stopper 232. The spring 230 and fluid stopper 232 enable the vaporizer 200 to modulate or control a fluid flow. The spring 230 and fluid stopper 232 may act as a valve that modulates fluid flow, e.g., within the first flow path 226 or from the reservoir through elongated member 226. The spring 230 may be made of any material, including metals, plastics, elastomeric elements, and the like. The fluid stopper 232, which may also be referred to as a plunger, may be made of any material, including metals, plastics, or elastomeric elements. An elastomeric element may refer to a polymer with viscoelasticity and generally having a low Young's modulus and high failure strain compared with other materials. Elastomeric elements may comprise rubbers, silicone (e.g., room temperature vulcanizing ("RTV") silicone), cured liquid silicone resin (e.g., NuSil MED-48xx series), and the like.

The spring 230 can be deformable. Further, the spring 230 can be elastic, e.g., may resume a resting state spontaneously after contraction, dilation, and/or distortion. The spring 230 can thus present a bias force. The bias force may maintain the flow modulator 228 in a default configuration (e.g., equilibrium, resting state, steady state configuration, etc.). In some instances, the bias force may maintain the flow modulator 228 in a closed configuration. The closed configuration may correspond to a resting state of the flow modulator 228, e.g., not under external forces. The closed configuration may correspond to an equilibrium state of the spring 230. In the closed configuration, fluid stopper 232 may block flow of liquid from the reservoir 208 through elongated member 226 to a vicinity of the heating element 220. In the closed configuration, the fluid stopper 232 may block flow of liquid within the first flow path 226.

Similar to vaporizer 100, vaporizer 200 can include an inner elongate member 229. Vaporizer 200 can further include an additional element 234, which may represent an extension of the inner elongated member 229. Alternatively, element 234 may represent an intermediary structure (e.g., tube, housing, etc.) configured to couple the heating element 220 to the inner elongated member 229. The proximal end of the inner elongated member 229 can be coupled (e.g., connected) to the reservoir 208. The distal end of the inner elongated member 229 may be coupled to the heating element 220, e.g., directly or via intermediary structures. The exit port 236 of the atomizer may be towards a chamber 216 of the vaporizer.

The fluid stopper 232 can be in communication with the inner elongated member 226 on one side and an air chamber 238 on the other side. The fluid stopper 232 may be in communication with the first flow path 226. In some instances, the fluid stopper 232 can be configured such that a force exerted along a displacement axis of the stopper 232 is smaller on the side of the inner elongated member 229 (e.g., first flow path 226) than on the side of the air chamber 238. For example, this can be achieved using a two-part plunger with two different cross-sectional diameters placed within a tube of similarly expanding cross-section as shown in FIG. 2. The portion of the plunger with the smaller cross-sectional diameter may be in contact with the elongated member side, or the liquid. The portion of the plunger with the larger cross-sectional diameter may be in contact with an air chamber side, or the air. The difference in the surface areas of the two sides (e.g., difference in a cross-sectional diameter) can enable the fluid stopper to act as a pressure amplifier.

In some instances, the air chamber 238 can be in communication with the chamber 216 of the outer elongate member 201 of the vaporizer 200. In some instances, the air chamber 216 may be in communication with a throat of a venturi tube 240. The venturi tube may be in communication with open air 218 and/or chamber 216. For example, an entrance of the venturi tube 240 may be in communication with open air 218 and an exit of the venturi tube 240 may be in communication with chamber 216. In some embodiments, the venture tube 240 can be connected to the air chamber 238 through a separate tube 242 for providing air thereto.

Figure 3:
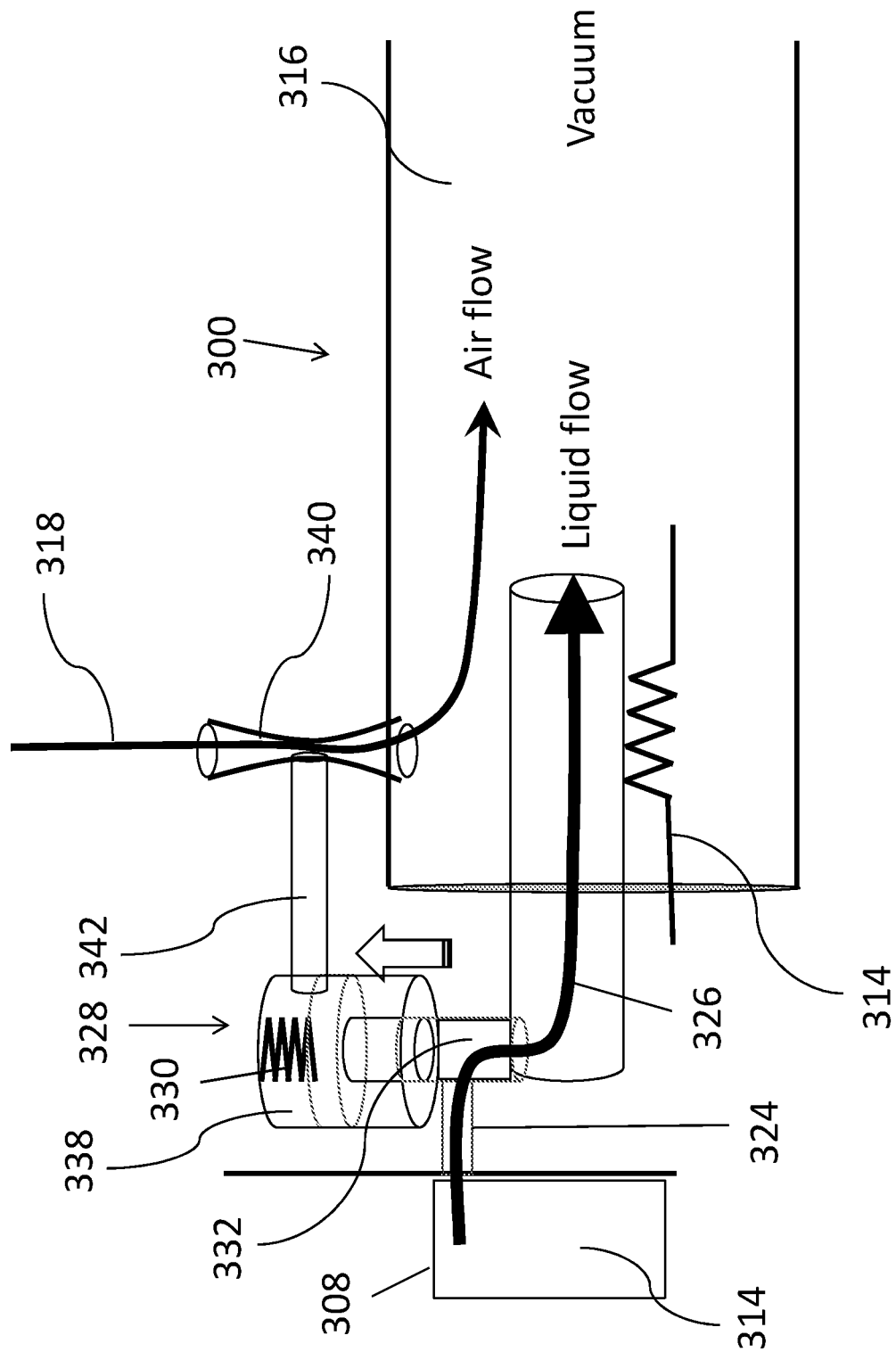
FIG. 3 illustrates an open configuration of a vaporizing device utilizing a spring, in accordance with embodiments.

FIG. 3 illustrates an open configuration of a vaporizing device 300. The open configuration may correspond to a configuration of the device 200 of FIG. 2 in response to an inhalation of a user. An inhalation of a user may create a vacuum in a chamber 316. The vacuum in the chamber 316 may establish an airflow path 318 into the chamber 316 via venturi tube 340. The airflow path 318 may refer to air traveling within the third flow path, previously described herein. The airflow into the chamber 316 may induce amplified vacuum within the throat of the venturi tube 340, which may be in communication with air chamber 338 via separate tube 342. In some instances, the airflow into the chamber 316 may induce amplified vacuum within the air chamber 338.

The vacuum within the throat of the venturi tube 340 may exert a force (e.g., upward force) on the fluid stopper 332. Alternatively or in addition, vacuum in chamber 316 may establish a vacuum within the inner elongated member 329. The vacuum within the inner elongated member 329 may exert a force (e.g., downward force) on the fluid stopper 332. The force exerted by the vacuum within the throat of the venturi tube 340 (or the air chamber 338) may be greater than a force exerted by the vacuum within the inner elongated member 329. The upward force exerted on the fluid stopper 332 may be greater than a downward force exerted on the fluid stopper 332 by an inhalation of a user. A pressure differential may be established across the fluid stopper 332, e.g., due to inhalation of a user. The pressure differential may cause the flow modulator 328 (e.g., the fluid stopper and/or spring) to slide to an open position, which may allow liquid from reservoir 308 to flow through the inner elongated member 329 and into a vicinity of heating element 320.

In some instances, an extent of the opening of the inner elongated member 329 may be proportional to a vacuum applied to chamber 316. In some instances, an extent of the opening of the inner elongated member 329 may be proportional to a vacuum applied by a user. In some instances, the configuration of the flow modulator 328 may correspond to a vacuum applied to chamber 316. In some instances, the configuration of the flow modulator 328 may depend on the vacuum applied by a user, e.g., by inhalation of the user. In some instances, the extent of the opening of the flow modulator 328 may be equal to the amount of vacuum applied to chamber 316.

Figure 4:
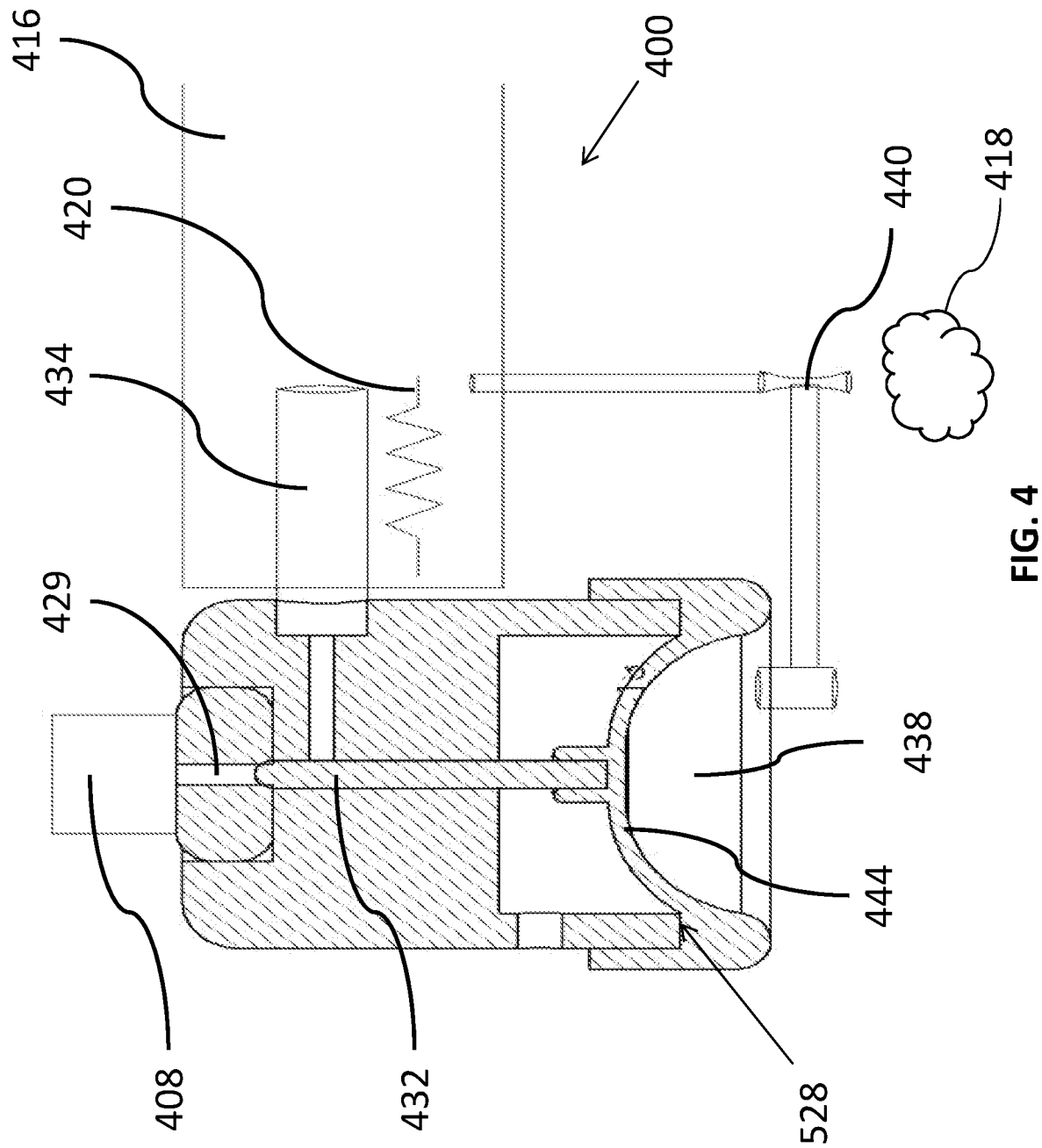
FIG. 4 illustrates a closed configuration of a vaporizing device utilizing a deformable membrane, in accordance with embodiments.

In some instances, the fluid flow modulator may comprise a deformable membrane, also referred to herein as a membrane. FIG. 4 illustrates a closed configuration of a vaporizing device 400 that is similar to device 100, but includes a deformable membrane 444 as part of the flow modulator 428. The deformable membrane 444 and fluid stopper 432 may enable a vaporizer 400 to modulate or control a fluid flow. The membrane 444 and fluid stopper 432 may act as a valve that modulates fluid flow, e.g., from the reservoir 408 through the inner elongated member 429, or within the first flow path. The fluid stopper 432 may be operably coupled to the deformable membrane 444. For example, the fluid stopper 432 may be directly connected to the deformable membrane 444. The fluid stopper 432 may be coupled to the membrane 444 removably or permanently. In some instances, a movement of the fluid stopper 432 may correspond to a movement of the deformable membrane.

The deformable membrane 444 may be made of any material, including metals, plastics, or elastomeric elements. Elastomeric element may refer to a polymer with viscoelasticity and generally having low Young's modulus and high failure strain compared with other materials. Elastomeric elements may comprise rubbers, silicone (e.g., room temperature vulcanizing ("RTV" silicone), cured liquid silicone resin (e.g., NuSil MED-48xx series), and the like. The membrane 444 may be deformable. The membrane 444 may be elastic, e.g., may resume a resting state spontaneously after contraction, dilation, and/or distortion.

The membrane 444 may present a bias force. The bias force may maintain the flow modulator 428 in a default configuration (e.g., equilibrium, resting state, steady state configuration, etc.). In some instances, the bias force may maintain the flow modulator 428 in a closed configuration. The closed configuration may correspond to a resting state of the flow modulator 428, e.g., not under external forces. In the closed configuration, the fluid stopper 432 may block flow of liquid solution from the reservoir 408 through the inner elongated member 426 to a vicinity of the heating element 420.

Element 434 may represent an extension of the inner elongated member 426. Alternatively, element 434 may represent an intermediary structure (e.g., tube, housing, etc.) configured to couple the heating element 120 to the elongated member, previously described elsewhere.

The proximal end of the inner elongated member 429 may be coupled (e.g., connected) to the reservoir 408. The distal end of the inner elongated member 429 may be coupled to a heating element 420, e.g., directly or via intermediary structures. The exit port of the atomizer may be towards a chamber 416 of the vaporizer 499.

The fluid stopper 432 may be in communication with the inner elongated member 429 on one side. An opposite side of the fluid stopper may be directly connected to the membrane which may be in communication with an air chamber 438. In some instances, the flow modulator 428 (e.g., fluid stopper and the elastomeric element) may comprise a design where a force exerted along a displacement axis of the flow modulator 428 is smaller on a side of the elongated member than on a side of the air chamber. For example, the plunger comprising a smaller cross-sectional diameter may be in contact with an inner elongated member side, or the liquid. A portion of the elastomeric element with a larger cross-sectional diameter may be in contact with an air chamber side, or the air. A difference in the surface areas of the two sides (e.g., difference in a cross-sectional diameter) may enable the valve to act as a pressure amplifier.

In some instances, the air chamber 438 may be in communication with a throat of venturi tube 440. Alternatively or in addition, the venturi tube 440 may be in communication with open air 418 and/or chamber 416. For example, an entrance of the venturi tube 440 (e.g., inlet) may be in communication with open air and an exit of the venturi tube 440 (e.g., outlet) may be in communication with the chamber.

Figure 5:
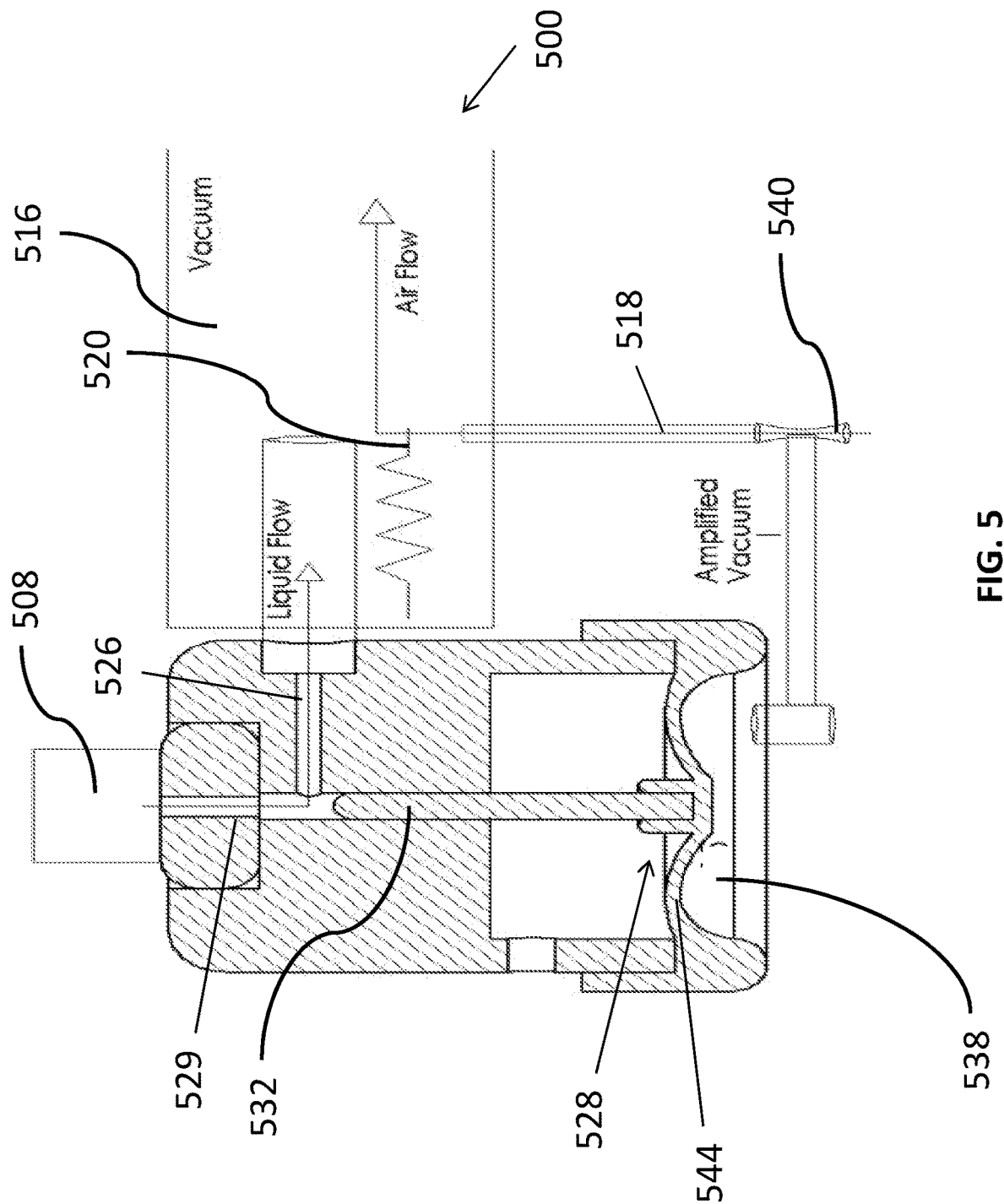
FIG. 5 illustrates an open configuration of a vaporizing device utilizing a deformable membrane, in accordance with embodiments.

FIG. 5 illustrates an open configuration of a vaporizing device 500 utilizing a deformable membrane. The open configuration may correspond to a configuration of the device 400 of FIG. 4 in response to an inhalation of a user. The inhalation of a user may create a vacuum in chamber 516. The vacuum in the chamber 516 may establish an airflow into the chamber via venturi tube 540. The air flow 518 from open air into the chamber 516 may induce amplified vacuum within the throat of the venturi chamber 540, which may be in communication with an air chamber 538. The vacuum within the throat of the venturi chamber 540 may exert a force (e.g., downward force) on the deformable membrane 544. The force exerted on the deformable membrane 544 may cause movement of the deformable membrane 544, and the fluid stopper 532, which is coupled to the membrane 544, in a direction of the force. The vacuum within the throat of the venturi chamber 540 may cause the flow modulator 528 (e.g., fluid stopper 532) to slide to an open position (e.g., down), which may allow liquid in the reservoir 508 to flow along flow path 526 through the inner elongated member 529 and into a vicinity of heating element 520. In some instances, an extent of the opening of the inner elongated member 528 may be proportional to a vacuum applied to chamber 516, e.g., by inhalation of a user. In some instances, an extent of the opening of the flow modulator 528 may be equal to a vacuum applied to chamber 516.

In some instances, the fluid flow modulators described herein may comprise a bi-metallic element. A bimetallic element as used herein may refer to any composite materials where two different metals are bonded together. The bimetallic element may also be referred to as a bimetallic composite throughout. The two different metals may comprise two different thermal expansion coefficients. The difference between the thermal expansion coefficients of the metals may cause the bi-metallic element to curl or flex along one or more axis when heated. The difference between the thermal expansion coefficients of the metals may cause the bi-metallic element to change configurations when heated. Heating energy may be provided by a heating element used in the vaporizer and/or by a separate heating element. The heating element may be triggered by a sensor (e.g., vacuum sensitive sensor) or a manual switch in the vaporizing device. Common metal pairs that can be employed include brass and steel, copper and steel, aluminum and polysilicon, or any metal pair that can be bonded and have dissimilar thermal expansion coefficients. In some instances, the vaporizer may comprise metallic valve elements comprising three or more metals. For example, the bi-metallic element may comprise two, three, four, five, six, seven, eight or more metals.

Figure 6B:
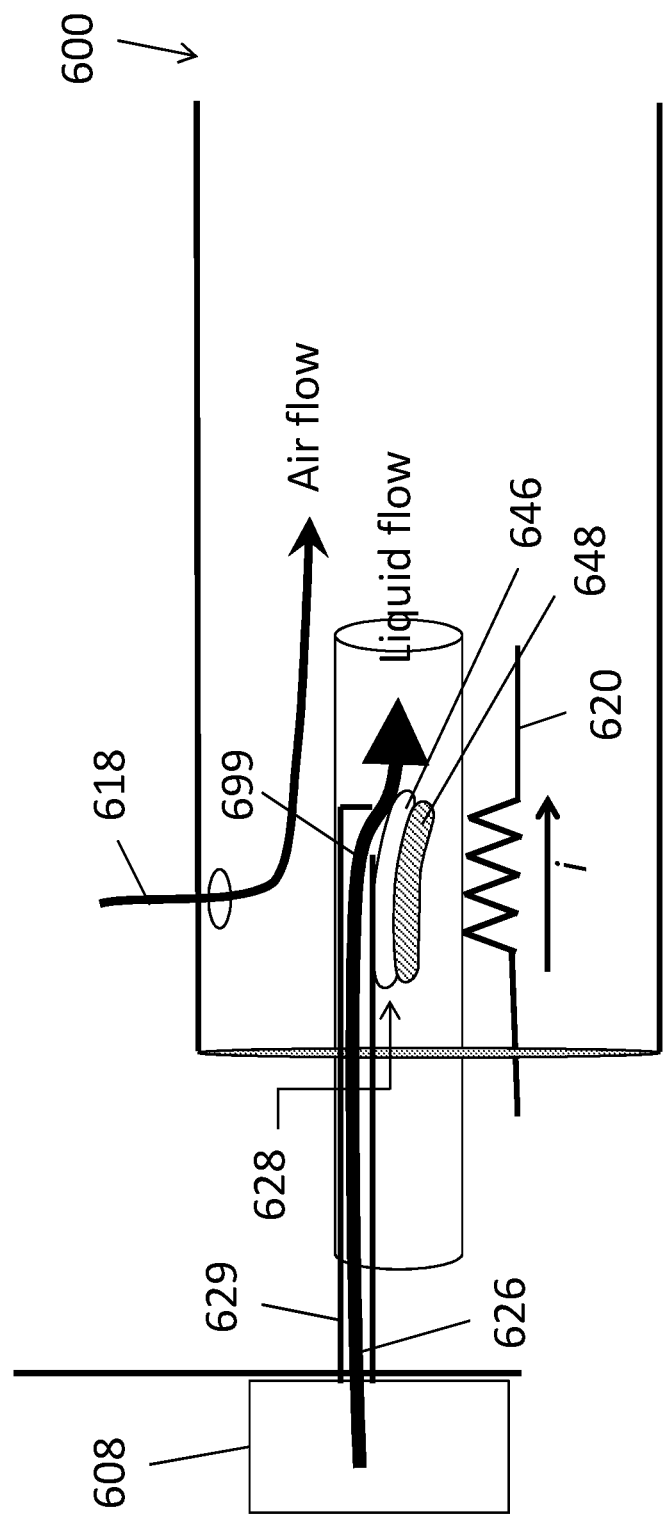

FIGS. 6A and 6B illustrate a closed configuration (FIG. 6A) and open configuration (FIG. 6B) of a vaporizer 600 including a flow modulator 628 comprising a bi-metallic valve element. The bi-metallic element may comprise a first metal 646 and a second metal 648. In the closed configuration (shown in FIG. 6A), the flow modulator 628 (e.g., composite metal or bi-metallic element) may physically block an exit of the inner elongated member 626. For example, fluid from reservoir 608 may flow through the inner elongated member 628. An opening, or exit of the inner elongated member 628 may be blocked by the flow modulator 628. For example, the metal 646 (the "first metal") closer to the opening 699 of the inner elongated member 629 may block the 699. In the closed configuration, the two metals 646, 648 may be of equal length, and the composite may prevent flow of fluid into a vicinity of the heating element 620.

In the open configuration (shown in FIG. 6B), the metal 646 closer to the opening 699 of the inner elongated member 629 can become longer than the metal 648 (the "second metal") further away from the opening 699 of the inner elongated member 629. The difference in length of the metals 646, 648 can bend the composite and expose the opening 699 of the inner elongated member 629, allowing liquid to flow therethrough along flow path 626.

The bi-metallic flow modulator 628 can change configurations (e.g., from closed to open) in response to an external stimuli (e.g., change in temperature), in response to a sensor, and/or in response to a user, as described above with respect to other embodiments. For example, a user may draw breath (e.g., suck) through a mouthpiece of the vaporizer 600. The action of the user may be sensed (e.g., by a pressure sensor or airflow sensor), which may activate the heating element 620. Heat generated from the heating element 620 may subsequently cause the bi-metallic flow modulator 628 to change configurations.

While a single metal 646 is shown blocking flow of fluid through the opening 699 in FIG. 6A, it is to be understood that both of the metals 646, 648 may block a flow of fluid. Alternatively or in addition, the bi-metallic element may be coupled to a separate and/or additional fluid stopping element that may block a flow of fluid. The separate fluid stopping element may change a configuration in correspondence to the bi-metallic element, e.g., in response to heat. For example, the bi-metallic element may be coupled to silicon and/or silicone oxide, similar to a MEMS valve as described below. While FIGS. 6A and 6B illustrate simplified configurations of the vaporizer, it is to be understood that any of the components of the vaporizers described throughout (e.g., venturi tubes) may be used in conjunction with the bi-metallic valve.

Figure 7A:
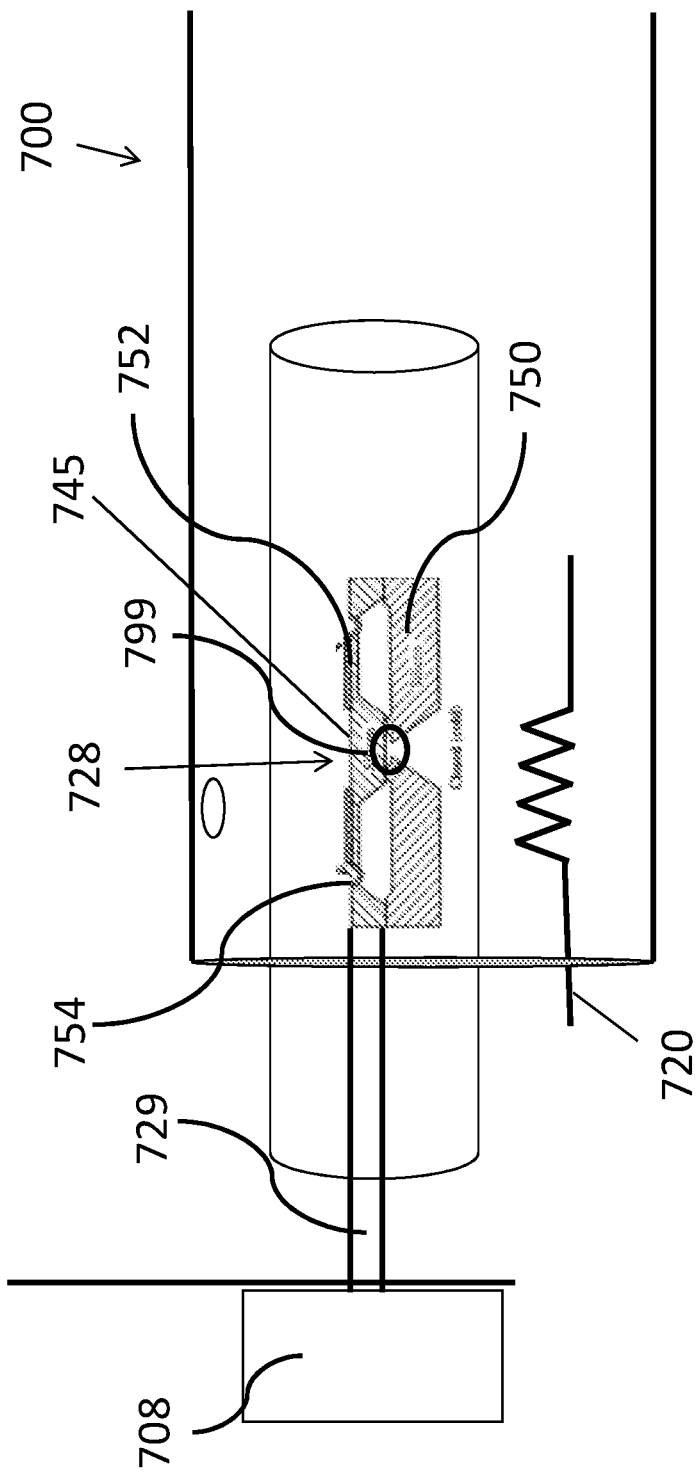
FIGS. 7A and 7B illustrate an open configuration (FIG. 7B) and closed configuration (FIG. 7B) of a vaporizer using microelectromechanical systems (MEMS) technology, in accordance with embodiments.
Figure 7B:
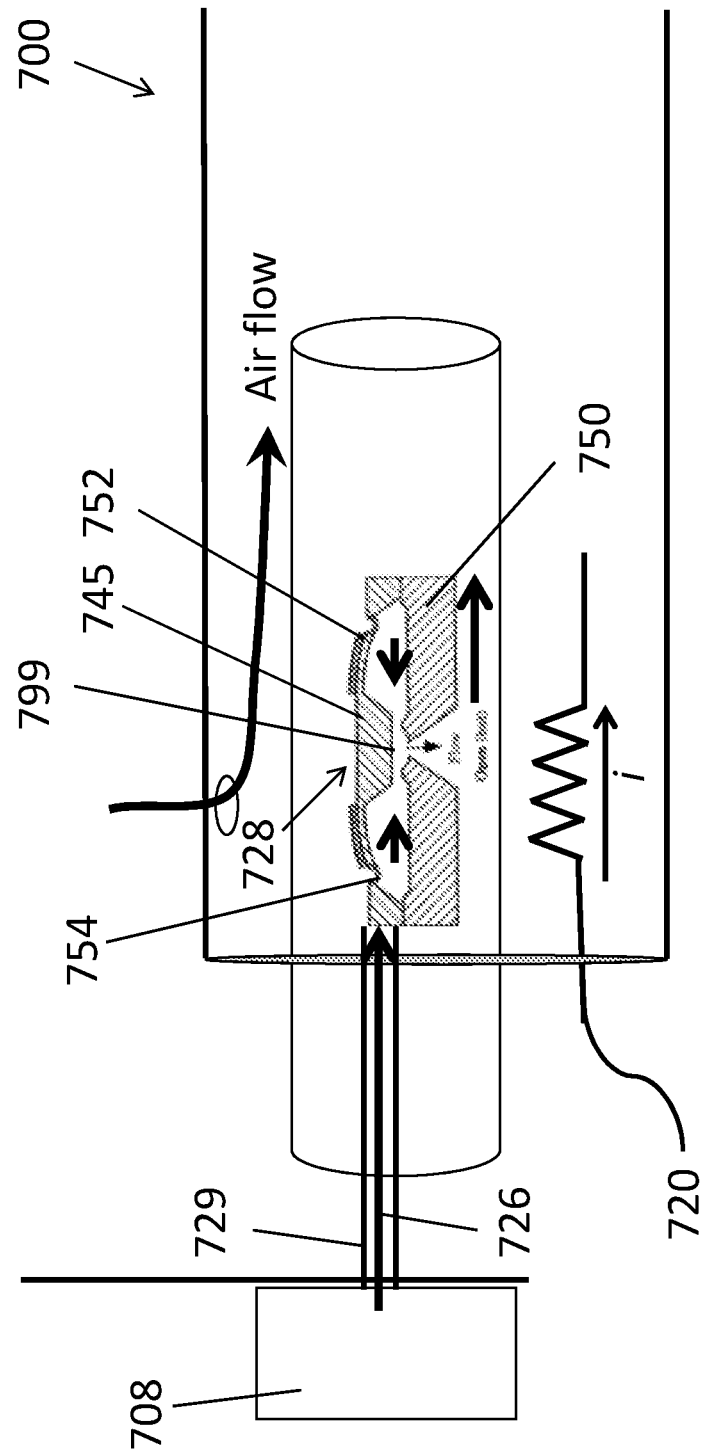

FIGS. 7A and 7B illustrate a closed configuration (FIG. 7A) and an open configuration (FIG. 7B) of a vaporizer 700 including a flow modulator 728 comprising a microelectromechanical systems (MEMS) valve. In some instances, the MEMS valve may be comprised of silicon 750, aluminum 752 and silicon oxide 754. While a MEMS configuration comprising silicon, aluminum, and silicone oxide is shown in FIGS. 7A and 7B, it is to be understood that FIGS. 7A and 7B is only illustrative, and many other MEMS configurations are possible.

In the closed configuration of FIG. 7A, the MEMs flow modulator 728 may block fluid flow from reservoir 708 through the inner elongated member 729. The opening 799 or exit of the inner elongated member 729 may be blocked by the MEMS flow modulator 728. Referring to FIG. 7B, when the flow modulator 728 is heated (e.g., by a heating element 720 in response to a user activating the vaporizer 700), the upper chamber wall 745 may deform due to differential expansion of aluminum 752 bonded to the silicon 750. The deformation can move the MEMs element out of the way of the opening 799, allowing fluid to flow from the reservoir 708 into or near the heating element 720.

While deformable elements comprising springs, deformable membranes, and bi-metallic elements have been primarily discussed herein, it is to be understood that the vaporizers of the present disclosure may utilize any deformable element. In some instances, the use of deformable elements or valves configured to control and/or modulate of fluid flow may enable utilization of novel atomizer designs.

FIGS. 8A and 8B illustrate a vaporizer 800 comprising an atomizer 804 including an inlet tube 834 for coupling the heating element to the inner elongated member described herein. In some instances, the vaporizer 800 may include the atomizer 804 coupled with a breath-modulated valve, or any of the components described herein, e.g., a venturi tube. In some instances, the inlet tube 834 may be a portion of the inner elongated member previously described above. Alternatively, the inlet tube 834 may be an intermediary element configured to couple the heating element 820 to an inner elongated member. The inlet tube 834 may allow natural flow (e.g., bulk flow, mass flow) of fluid (e.g., from the reservoir) onto a vicinity of the heating element 820, where the liquid can then vaporize. In some instances, a flow of fluid from the reservoir onto a vicinity of the heating element may be aided by other forces, e.g., vacuum created from an inhalation of a user, an external force (e.g., that from a cocked spring, fluid pumps, etc.), and/or gravity.

Figure 8D:
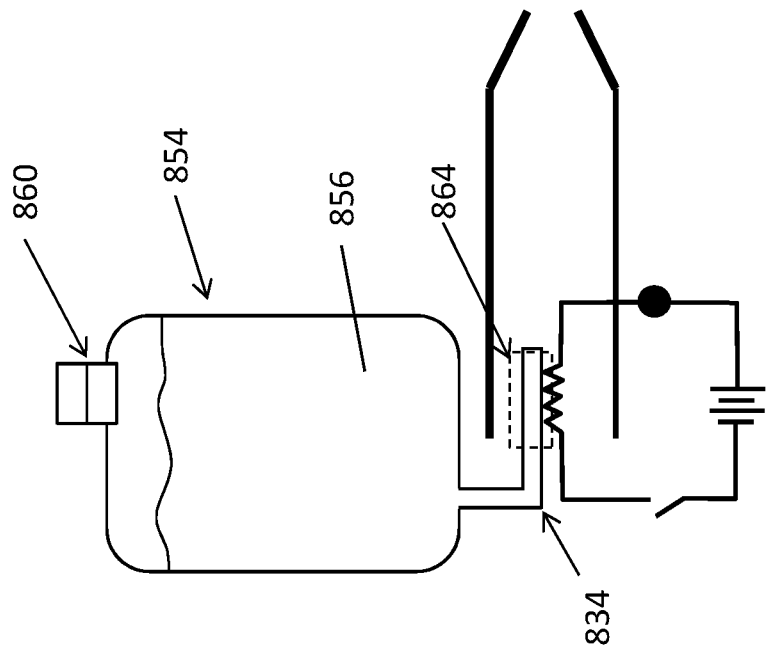
FIGS. 8C and 8D schematically illustrate one example of a portion of a vaporizer including a fluid flow modulator that controls flow of a vaporizable solution from a reservoir to a heater (e.g., a heater portion of an atomizer) by regulating the pressure (e.g., air pressure or fluid pressure) in the reservoir. In the example of FIG. 8C the reservoir is open to atmosphere, allowing vaporizable fluid to flow (alternatively, the pressure may be increased relative to surrounding/atmosphere)
Figure 8C:
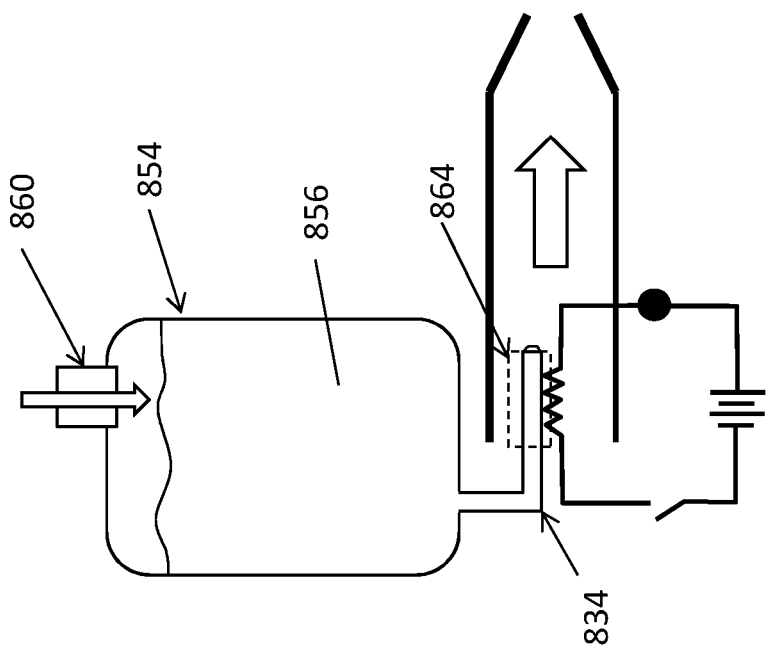

As mentioned, any of the reservoirs described herein may be pressurized, to bias fluid flow out of the reservoir, or may include a pressure regulator (e.g., as part of a fluid flow modulator) to increase and/or decrease the pressure in the reservoir either actively or passively. For example, FIGS. 8C and 8D illustrate an example in which a fluid reservoir 854 holding a vaporizable fluid material 856 includes a pressure regulator 860 (shown schematically in FIGS. 8C and 8D). In this example, the vaporizable fluid may enter and leave the atomizer 864 (shown in this example as a region of the elongate tube/inlet tube 834) as the pressure in the reservoir is regulated to be greater than atmosphere (shown in FIG. 8C), or approximately the same as atmosphere (FIG. 8D). If the vaporize is configured so that gravity (or some other force, e.g., magnetic, etc.) is driving flow of the vaporizable fluid, opening the reservoir to atmosphere (e.g., the pressure regulator is a valve that opens to atmosphere) may allow flow into the heater region 864, while closing it may prevent flow. In FIG. 8D, for example, the pressure regulator 860 is closed and/or sets the pressure in the reservoir to be approximately the same as (+/- the resistance to flow due to the elongate tube/inlet tube 834). As mentioned above, a flow modulator can include a mechanisms configured to control the flow of fluid through surface tension rather than with a valve.

The inlet tube 834,834 may be made, for example, of a polymer or a metal, such as stainless steel. In some instances, the inlet tube 834 can include a coating thereon. For example, the inlet tube 834 can be coated with an insulating material. In some instances, the inlet tube 834 can be oxidized to form a thin insulating coating. The coating may overcome or guard against potential shorting issues associated with operation of the vaporizing device 800.

The heating element 820 may be coupled to the inlet tube 834. The heating element may include any element that is configured to generate heat to vaporize liquid from the reservoir, as previously described herein. For example, the heating element 820 may comprise an electrical heater wire or a coil. In some instances, the electrical heater wire may be a nichrome wire. In some instances, the heating element 820 may be wrapped around the inlet tube 834. The heating element 820 may be positioned anywhere along a length of the tube, e.g., near a proximal end 858 of the inlet tube 834.

In some instances, the heating element 834 may be non-solderable. For example, an electrical heater wire may be non-solderable. In some instances, reliable electrical connections (e.g., between the inlet tube 834 and the heating element 820) may be achieved by crimping the inlet tube 834 (e.g., stainless hypotube, e.g., 0.012" internal diameter) around each free end of a coil making up the heating element 820. Insulated copper wire leads 817, in turn, may be soldered to the short lengths of crimped inlet tube 834. Alternatively, reliable electrical connections may be achieved by directly spot welding wire leads to the heater wire.

The heating element 820 (e.g., electrical heater wire) may have a diameter, for example, of equal to about or less than 0.001, 0.002, 0.05, 0.075, 0.01, 0.0125, 0.015, 0.02, 0.025, 0.03, 0.035, 0.04, 0.045, or 0.05 inches. For example, the heating element or wire may be equal to about or greater than 0.001, 0.002, 0.05, 0.075, 0.01, 0.0125, 0.015, 0.02, 0.025, 0.03, 0.035, 0.04, 0.045, or 0.05 inches in diameter.

The heating element 820 (e.g., wire) may be wound around the tube with a predetermined spacing. For example, the spacing may be equal to about or less than 0.001, 0.002, 0.003, 0.004, 0.005, 0.006, 0.007, 0.008, 0.009, 0.01, 0.012, 0.014, 0.016, 0.018, 0.02, 0.025, 0.03, 0.035, 0.04, 0.045, or 0.05 inches in length. For example, the spacing may be equal to about or greater than 0.001, 0.002, 0.003, 0.004, 0.005, 0.006, 0.007, 0.008, 0.009, 0.01, 0.012, 0.014, 0.016, 0.018, 0.02, 0.025, 0.03, 0.035, 0.04, 0.045, or 0.05 inches in length. In some instances, the spacing may range from about 0.005 to 0.01 inches in length. In some instances, the spacing may range from about 0.001 to 0.02 inches in length. A length of the wire and material of construction may determine circuit resistance. In some instances, a resistance of the vaporizing device (e.g., atomizer) may be equal to about or greater than 0.2, 0.5, 1, 2, 3, 4, 5, 6, 7, 8, 9, or 10 ohms. In some instances, a resistance of the vaporizing device (e.g., atomizer) may be equal to about or lesser than 0.2, 0.5, 1, 2, 3, 4, 5, 6, 7, 8, 9, or 10 ohms. An external source (e.g., battery) may provide power into the heater wire. In some instances, a power range of the external source may be from about 0 W to 10 W. In some instances, a power range may be from about 0.5 W to 10 W. In some instances, a power range may be from about 1 W to 10 W. In some instances, a power range may be from about 0.5 W to 12 W. In some instances, a power range may be from about 0.5 W to 15 W.

The inlet tube 834 may comprise a proximal tip 858 that is sealed or open. In some instances, the inlet tube 834 may comprise one or more vent slots 860 extending along an outer wall thereof (see FIG. 8B). For example, the inlet tube 834 may include one, two, three, four, five, six, seven, eight, nine, ten or more vent slots 960 along the outer wall. The vent slots 860, also referred to herein as slots, may be equidistant from one another. For example, the inlet tube 834 of FIG. 8 may comprise four equidistant slots 860 near the proximal tip 858 of the tube. Alternatively, the slots 860 may be arranged in any configuration or pattern and may not be equidistant from one another. The vent slots 860 may comprise any size. For example, the slots 860 may be equal to about or less than 0.05, 0.075, 0.1, 0.125, 0.15, 0.2, 0.25, 0.03, 0.4, or 0.5 inches in length and/or width. For example, the slots 860 may be equal to about or greater than 0.05, 0.075, 0.1, 0.125, 0.15, 0.2, 0.25, 0.03, 0.4, or 0.5 inches in length and/or width. In some instances, the slots 860 may be equal to or greater than about 0.125 inches in length and 0.02 inches in width. In some instances, the slots 860 may be equal to about or greater than 0.125 inches in width and 0.02 inches in length. Each of the vent slots 860 on the inlet tube 834 may be of the same size. In some instances, the vent slots 860 along the inlet tube 834 wall may be of different sizes. In some instances, the inlet tube 834 may comprise a plurality of open holes along its outer wall. In some instances, the inlet tube 834 may comprise a plurality of pores along its outer wall. In some instances, the inlet tube 834 may be porous.

The vent slots 860, pores, and/or open holes may be configured to release fluid. For example, fluid from a reservoir may pass through the inlet tube 834 and be released through the vent slots 860. In some instances, the heating element 820 may be coupled to the vent slots 860. For example, a heating element 820 (e.g., coils and/or wires) may pass along the vent slots 860 of the inlet tube 834. The heating element 820 may cover the vent slots 860. Alternatively or in addition, the heating element 820 may be coupled near the vent slots 860, but may not directly cover the vent slots 860. Fluid released through the vent slots 860 may rapidly heat and vaporize upon encountering the heating element 820 (e.g., coming near the heating element 820 and/or contacting the heating element 820). In some instances, fluid passing by the heating element 820 may rapidly heat and boil. Heated liquid (e.g., within the inlet tube 834) may exit into chamber 816. Depending on liquid flow rates and power input (e.g., into a heating element 820 via a power source), the liquid may evaporate into the air present in the chamber 816 or may boil and mix with the air in the chamber 816. Air in the chamber 816 may enter through any existing opening. For example, air may enter through, or from, port 862. In some instances, the port 862 may comprise, or be coupled to a venturi tube, previously described herein. In either instance, upon mixing with the colder air entering from port 862, the evaporated or boiled materials may condense downstream in chamber 816 and can form a thick vapor cloud that the smoker can inhale through proximal mouthpiece 864.

In some instances, the inlet tube 834 may be non-vented. For example, the inlet tube 834 may not comprise any vent slots on the side wall thereof. In such a case, the inlet tube 834 without vent slots may comprise an open tip 858. In some instances, the heating element 820 (e.g., heating wire) may be wrapped around the inlet tube 834 near the tip 858 (e.g., near its exit, near the open tip, etc.). Fluid passing by the heating element 820 may rapidly heat and vaporize upon passing through a section of the inlet tube 834 that is coupled to the heating element 820. Vapor that is generated may be released through the open tip 858. In some instances, fluid passing by the heating element 820 may rapidly heat and boil. Heated liquid (e.g., within the inlet tube 834) may exit into chamber 816. Depending on liquid flow rates and power input (e.g., into a heating element via a power source), the liquid may evaporate into the air present in the chamber 816 or can boil and can mix with the air in the chamber 816. In either instance, upon mixing with the colder air entering from port 862, the evaporated or boiled materials can condense downstream in chamber 816 and can form a thick vapor cloud that the smoker can inhale through mouthpiece 864.

Air (either ambient air, or air from a venturi element previously described elsewhere) may enter into chamber 816 through inlet port 862. The inlet port may comprise a predetermined diameter. For example, the inlet port diameter may be equal to about or greater than 0.01, 0.02, 0.03, 0.04, 0.05, 0.06, 0.07, 0.08, 0.09, 0.1, 0.12, 0.14, 0.16, 0.18, 0.2, 0.3, 0.4, or 0.5 inches. For example, the inlet port diameter may be equal to or lesser than about 0.01, 0.02, 0.03, 0.04, 0.05, 0.06, 0.07, 0.08, 0.09, 0.1, 0.12, 0.14, 0.16, 0.18, 0.2, 0.3, 0.4, or 0.5 inches.

The air may enter into the chamber 816 with a rate of airflow. The rate of airflow may correspond to a rate of airflow in response to an inhalation of a user. In some instances, the rate of airflow may be equal to or greater than about 1 L/min, 2 L/min, 3 L/min, 5 L/min, 10 L/min, 15 L/min, 20 L/min, 30 L/min, 40 L/min, 50 L/min, 60 L/min, 70 L/min, 80 L/min, 90 L/min, 100 L/min, 120 L/min, 140 L/min, 160 L/min, 180 L/min, or 200 L/min. In some instances, a rate of airflow may be equal to or lesser than about 1 L/min, 2 L/min, 3 L/min 5 L/min, 10 L/min, 15 L/min, 20 L/min, 30 L/min, 40 L/min, 50 L/min, 60 L/min, 70 L/min, 80 L/min, 90 L/min, 100 L/min, 120 L/min, 140 L/min, 160 L/min, 180 L/min, or 200 L/min. In some instances, a rate of airflow may range from about 5 L/min to 100 L/min, 10 L/min to 140 L/min, or 10 L/min to 100 L/min. The rate of airflow described herein may be applicable and relevant to any of the embodiments described throughout the present disclosure.

Figure 9:
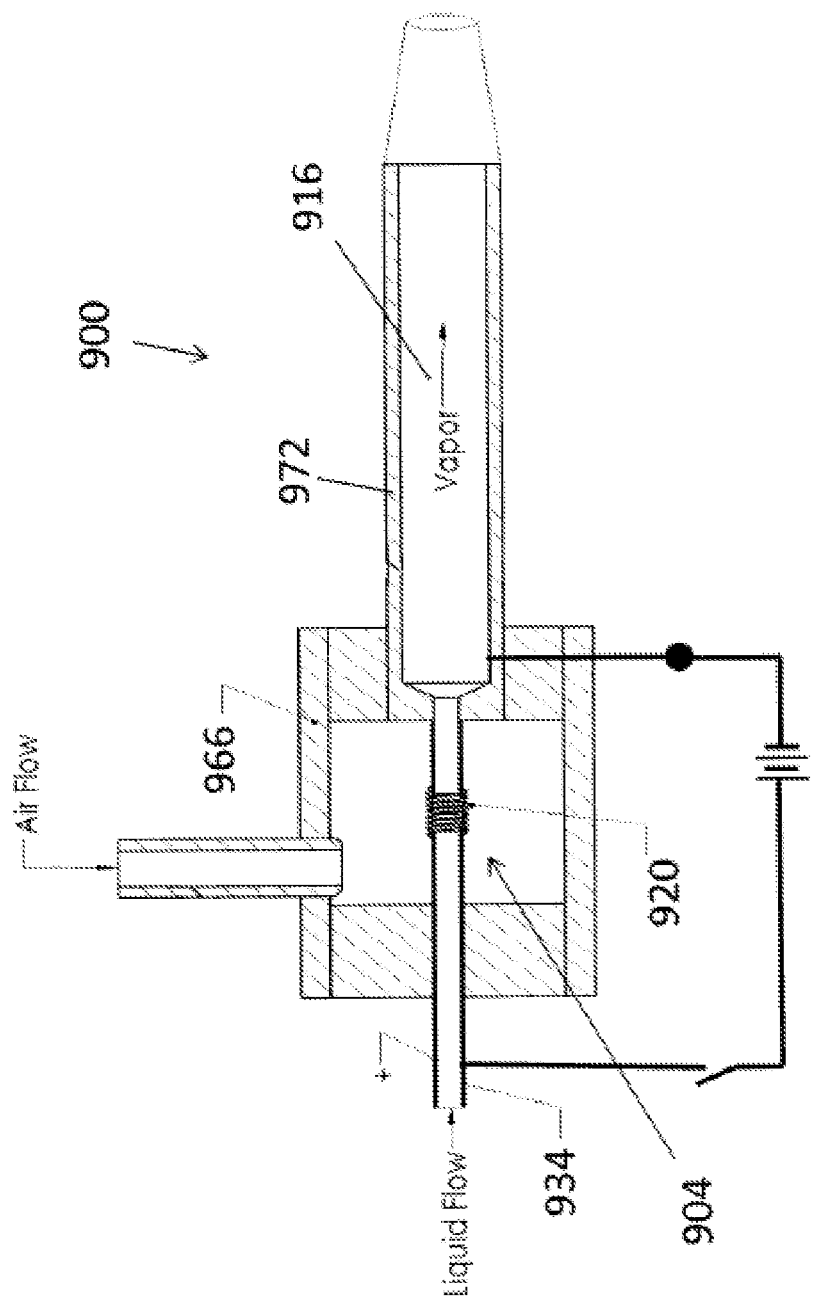
FIG. 9 illustrates a vaporizing device comprising an air-in-coil atomizer, in accordance with embodiments.

FIG. 9 illustrates a vaporizing device 900 including an air-in-coil atomizer 904 comprising an inlet tube 934 (similar to inlet tube 834). In some instances, the vaporizer 900 may include the atomizer 904 coupled with a breath-modulated valve, or any of the components described throughout, e.g., venturi tube. The air-in-coil atomizer 904 may include a coil that is coupled (e.g., electrically coupled) to the inlet tube 934 only at one end. In some instances, the inlet tube 934 may be a portion of the inner elongated member previously described herein. Alternatively, the inlet tube 934 may be an intermediary element configured to couple the heating element 920 to an inner elongated member, substantially as described above. In some instances, the air-in-coil atomizer 904 includes a coil that is coupled to the inlet tube 934 at one end and is coupled to a different element at another end. In such an embodiment, the inlet tube 934 and the different element may be electrically insulated. In some instances, the air-in-coil atomizer includes a coil that is coupled to the inlet tube 934 at one end and is coupled to an exit or outlet tube 972 at another end. The inlet tube 934 and the outlet tube 972 may be electrically insulated.

In some instances, the air-in-coil atomizer 904 may enhance a connectivity of heating element 920 (e.g., heater wire). For example, the air-in-coil atomizer 904 may avoid the use of crimped or spot-welded connections, previously discussed herein. In some instances, the heating element 920 (e.g., coil) may be in intimate contact with the inlet tube 934 configured for receiving a fluid at one end. Further, the outlet tube 972 can include a chamber 916 for releasing vapor on the other. In some instances, both the inlet tube 934 and outlet tube 972 may be metallic and an electrical connection may be made to the inlet tube 934 and outlet tube 972, thereby energizing the heating element (e.g., the coil). The air-in-coil atomizer 904 may circumvent electrical shorting issues between the coil and inlet tube 934. For example, the coil may only contact the inlet tube 934 on one end and may avoid shorting of circuity of the vaporizing device. For example, direct electrical connections may be made on the outside of the inlet tube 934 and chamber 916 (e.g., outlet tube 972).

In some instances, an inlet tube 934 and outlet tube 972 (e.g., metallic chamber or tube) may be simultaneously coaxially connected to an insulating hollow housing 966, thereby not being in electrical contact with one another (e.g., electrically insulated from one another). For example, the inlet tube 934 and outlet tube 972 may protrude into the insulating hollow housing 966 coaxially and in close proximity of each other but may not be touching. The housing 966 may be made of any insulating material, e.g., fibers, glass, polymers, or silicone rubbers.

In some instances, a coil of heater wire 920 may be separately formed. For example, 0.01" of nichrome wire may be wound around an undersized mandrel. The coil may then be slipped around the tip of the inlet tube 934, as well as the tip of the outlet tube 972. In some instances, a gap may be left in-between the inlet tube 934 and the outlet tube 972, which may be coupled together by the wire of the heating element 920. For example, a gap equal to or greater than about 0.001", 0.002", 0.005", 0.01", 0.02", 0.05", 0.1", 0.2", 0.3", 0.4", or 0.5" may be left between the inlet tube and the exit tube. For example, a gap equal to or less than about 0.001", 0.002", 0.005", 0.01", 0.02", 0.05", 0.1", 0.2", 0.3", 0.4", or 0.5" may be left between the inlet tube and the exit tube. For example, a gap between about 0.001", 0.002", 0.005", 0.01", 0.02", 0.05", 0.1", 0.2", 0.3", 0.4", or 0.5" may be left between the inlet tube 934 and the outlet tube 972. In some instances, the gap may be between about 0.005" and 0.01". The coil may be suspended in free space (e.g., within the gap). In some instances, the coil may be wound with no spacing. However once slipped onto the tubes (e.g., 934 and 972), a gap may be created by adjusting a fit (e.g., interference fit) between the tubes 934, 972.

Figure 10A:
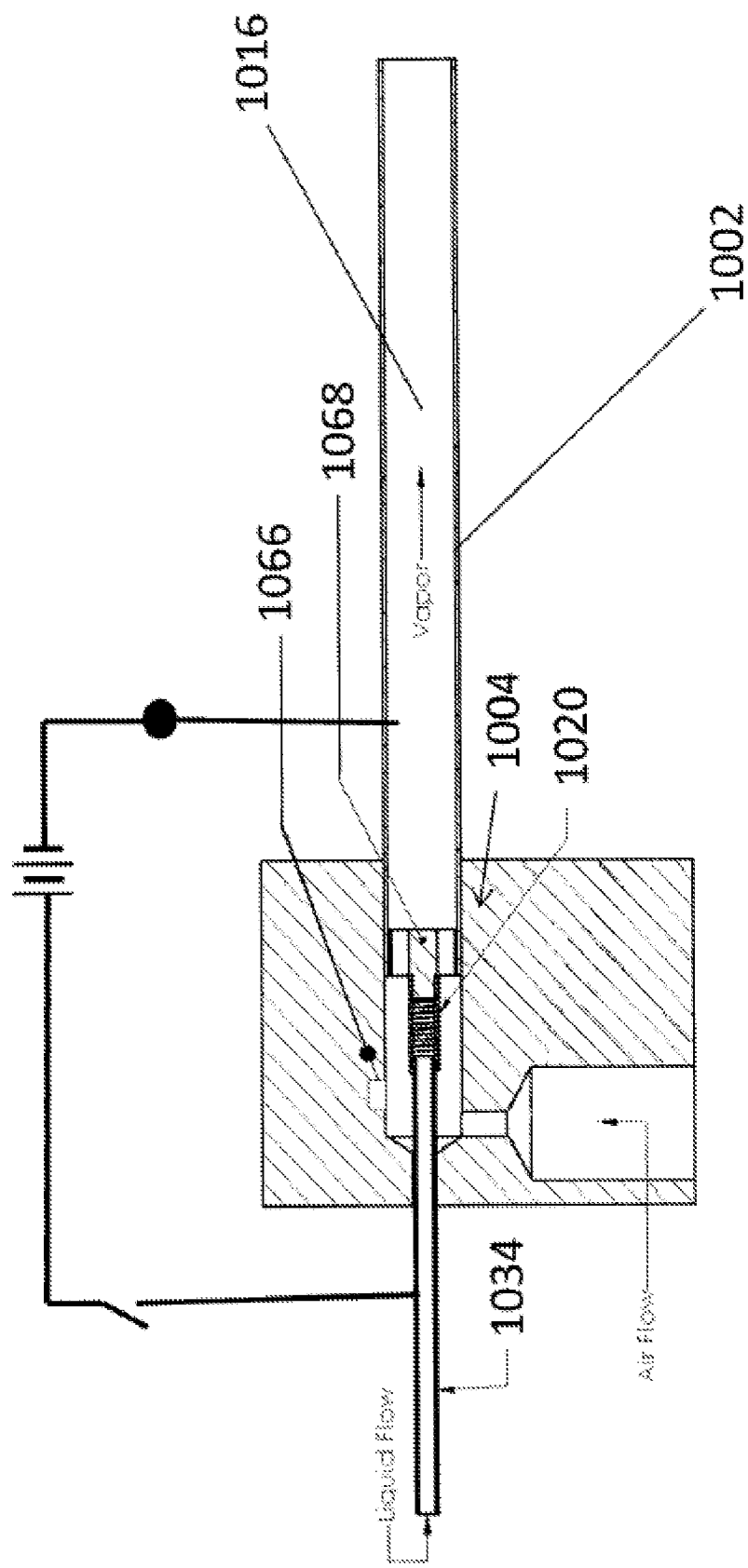
FIGS. 10A and 10B illustrate a vaporizing device comprising an air-over-coil atomizer, in accordance with embodiments.
Figure 10B:
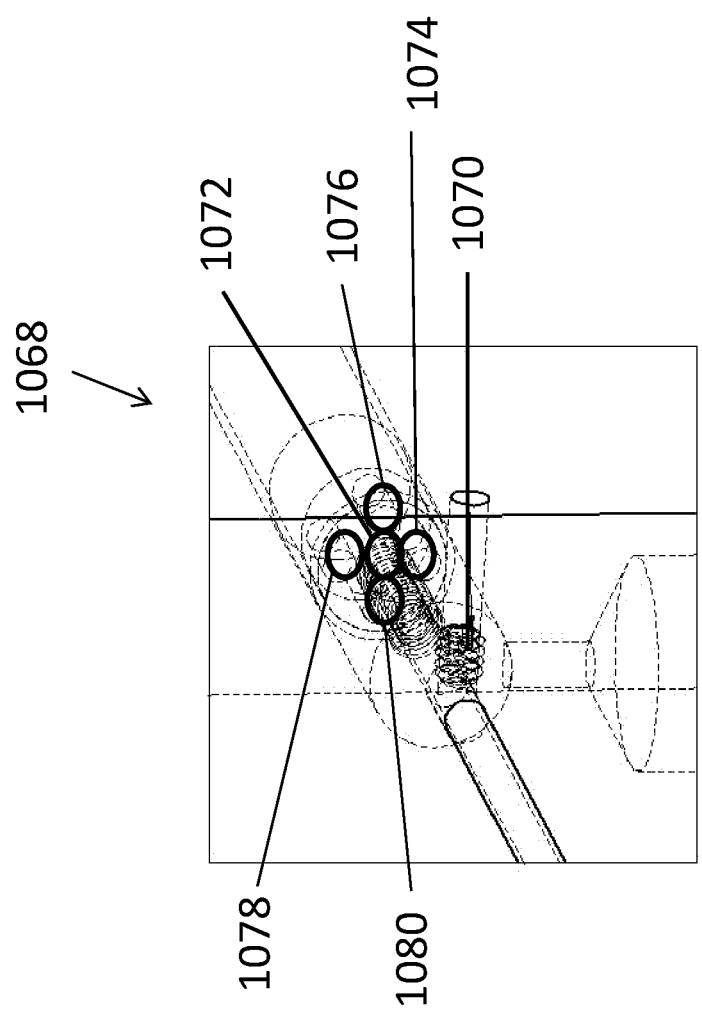

FIGS. 10A and 10B illustrate a vaporizing device 1000 comprising an air-over-coil atomizer 1004, in accordance with embodiments. In some instances, the vaporizer 1000 may comprise the atomizer 1004 coupled with a breath-modulated valve or any of the components described throughout, e.g., venturi tube. The air-over-coil atomizer 1004 may be configured to pass liquid (e.g., from a liquid reservoir) and generate vapor without the liquid contacting a heating element 1020 (e.g., coil). The air-over-coil atomizer 1004 may be configured to pass liquid (e.g., from a liquid reservoir) and generate vapor without the liquid passing through a heating element (e.g., coil). The air-over-coil atomizer 1004 thus may render it unnecessary for heated liquid to force its way between coils 1020 to stimulate evaporation. The air-over-coil atomizer 1004 design may improve air exchange with a heated liquid. For example, air may flow over the heated coil containing heated liquid, causing the liquid to evaporate.

The air-over-coil atomizer 1004 can include an inlet tube 1034 and a diffusor 1068 pressed into a chamber 1016. The tube 1034, diffusor 1068, and or the chamber 1016 may comprise metal or may be made of metallic components. In some instances, the inlet tube 1034 may be a portion of the inner elongated member previously described herein. Alternatively, the inlet tube 1034 may be an intermediary element configured to couple the heating element 1020 to an inner elongated member, substantially as described above. In some instances, the inlet tube 1034 and outlet tube 1002 may be both connected coaxially to a housing 1066 made of an insulating material. In some instances, the inlet tube 1034 and the diffusor 1068 may protrude into housing 1066 but may not be allowed to touch each other. A relative position of the inlet tube 1034 and the diffusor 1068 may be secured, e.g., via setscrews 1070. For example, the setscrews 1077 on the housing 1066 may impinge on the inlet tube 1034, the diffusor 1068, and or the chamber 1016 and secure a relative position of each of the components. In some instances, electrical connections may be made on each setscrew, or, alternatively on the inlet tube 1034 and/or chamber 1016 (e.g., exit tube) themselves.

The metallic diffusor 1016 may comprise a configuration of channels that allow thorough mixing of vaporized liquid and air streams. The mixing of the vapor, hot liquid, boiling liquid, and/or air streams may enhance and/or promote condensation of vapor. Referring to FIG. 10B, in some instances, the diffusor 1068 may comprise one channel (e.g., a center channel) 1072 for travel or flow of vapor. In some instances, the diffusor 1068 may include four channels 1074, 1076, 1078, 1080 for travel or flow of air. In some instances, the four channels configured to allow airflow may be located at a periphery of the channel configured to allow flow of vapor. Alternatively, the diffusor 1068 may comprise one, two, three, four, five or more channels each for passage of vapor and/or air. At an exit of the channels (e.g., of the diffusor 1068) into chamber 1016, mixing may promote and enhance condensation of the vapor. The air and/or vapor may continue to mix and condense as it passes through diffusor 1068 and into the chamber 1016. In some instances, the diffusor 1068 may be configured such that there is turbulent mixing between vapor and air.

The air-over-coil atomizer 1004 may allow for closer coil spacing. For example, since it may not be necessary for air to flow into the coil of the air-over-coil atomizer 1004 for mixing, the coil spacing may be as close as possible. A liquid (e.g., low viscosity hot liquid) may easily pass through small gaps within the coil spacing. Since vaporization may only occur at the coil, air may only need to flow around an outside of the coil to drive evaporation. Having to flow air inside the coil at the same time liquid is trying to enter the coil (e.g., pass through the coil) may create an unstable condition where airflow or liquid flow may dominate.

In some instances, a closer coil spacing may promote efficient heating of liquid in a vicinity of the atomizer 1004 (e.g., heating element, coil, etc.). The coil may be wound around the tube with a predetermined spacing. For example, the spacing may be equal to about or less than 0.001, 0.002, 0.003, 0.004, 0.005, 0.006, 0.007, 0.008, 0.009, 0.01, 0.012, 0.014, 0.016, 0.018, 0.02, 0.025, 0.03, 0.035, 0.04, 0.045, or 0.05 inches in length. For example, the spacing may be equal to about or greater than 0.001, 0.002, 0.003, 0.004, 0.005, 0.006, 0.007, 0.008, 0.009, 0.01, 0.012, 0.014, 0.016, 0.018, 0.02, 0.025, 0.03, 0.035, 0.04, 0.045, or 0.05 inches in length. In some instances, the spacing may range from about 0.005 to 0.01 inches in length. In some instances, the spacing may range from about 0.001 to 0.02 inches in length. A length of the wire and material of construction may determine circuit resistance. In some instances, a resistance of the vaporizing device (e.g., atomizer) may be equal to about or greater than 0.2, 0.5, 1, 2, 3, 4, 5, 6, 7, 8, 9, or 10 ohms. In some instances, a resistance of the vaporizing device (e.g., atomizer) may be equal to about or lesser than 0.2, 0.5, 1, 2, 3, 4, 5, 6, 7, 8, 9, or 10 ohms.

In some instances, a coil of heater wire may be separately formed. For example, 0.01" of nichrome wire may be wound around an undersized mandrel. The coil may subsequently be slipped around a tip (e.g., proximal end, exit portion, etc.) of the inlet tube 1034 as well as the diffusor 1068 (e.g., connecting for instance to a tube protruding from the center channel 1072). In some instances, a gap (e.g., 0.1") may be left between the inlet tube 1034 and the diffusor 1068, allowing the coil to be suspended in the free space between the inlet tube 1034 and the diffusor 1068. In some instances, the coil may be wound with no spacing. However, once slipped onto the tubes (e.g., tube 1034 and a tube of the diffusor 1068), a gap, or spacing may be created by adjusting a fit (e.g., interference fit) between the tubes.

Figure 11:
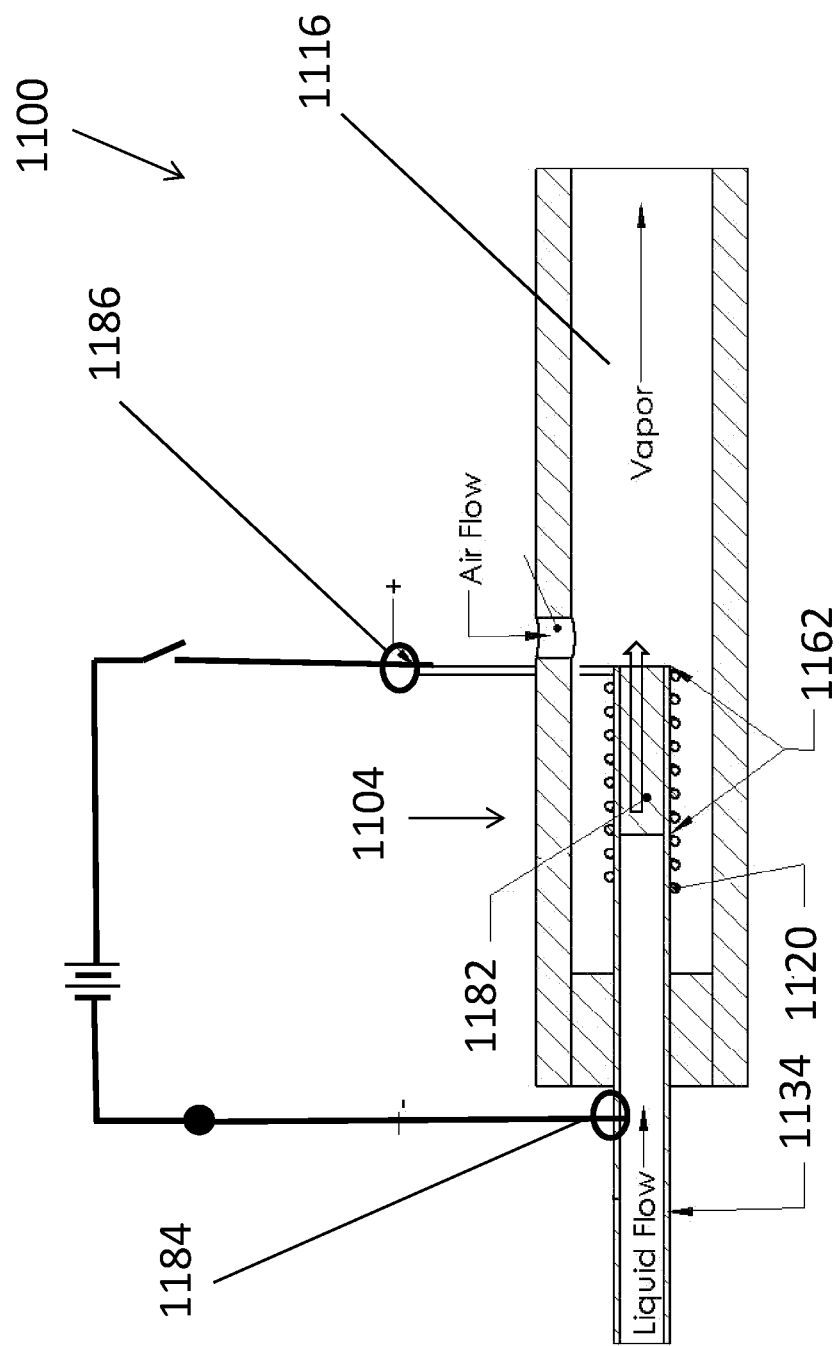
FIG. 11 illustrates a vaporizing device comprising a porous filter atomizer, in accordance with embodiments.

FIG. 11 illustrates a vaporizing device 1100 comprising a porous filter atomizer 1104, in accordance with embodiments. In some instances, the vaporizer 1100 may comprise the porous filter atomizer 1104 coupled with a breath-modulated valve or any of the components described throughout, e.g., venturi tube. The porous filter atomizer 1104 can include a porous element 1182 installed on a heated region 1162 of inlet tube 1134. The porous filter element 1182 may also be referred to as a porous filter herein. In some instances, the inlet tube 1034 may be a portion of the inner elongated member previously described herein. Alternatively, the inlet tube may be an intermediary element configured to couple the heating element 1120 to an inner elongated member, substantially as described above.

In some instances, the porous filter element 1182 may be located on a region of the inlet tube 1134 that comprises a heating element 1120, e.g., a coil. For example, the heating element 1120 may reside over on portions of the inlet tube 1134 that comprise the porous filter element 1120. In some instances, the porous filter element 1182 may be located throughout the inlet tube 1134. In some instances, the porous filter element 1182 may be used as a heater (e.g., instead of a separate heating element 1120 such as a coil).

The porous filter element 1182 may be externally insulated. In some instances, an outside of the inlet tube 1134 may comprise an electrically insulating coating 1162 (e.g., ceramic adhesive). In some instances, the electrically insulating coating 1162 may be present on only portions of the inlet tube 1134, e.g., on areas that comprise the porous filter. In some instances, the heating element 1120, such as a heated coil, may reside over the electrical insulating coating. In some instances, a portion of the coil may reside on a non-insulated tube section, while another portion of the coil may protrude from the chamber 1116.

The porous filter element 1182 may mitigate unevaporated liquid from entering chamber 1116. For example, the pores in the filter element 1182 may be sized such that gas may escape or pass through the pores while liquid is not able to escape. Remaining liquid within the inlet tube 1134 may be further heated for evaporation. For example, a size of pores on a porous filter may be equal to or greater than about 0.0005 inches, 0.001 inches, 0.002 inches, 0.003 inches, 0.004 inches, 0.005 inches, 0.006 inches, 0.007 inches, 0.008 inches, 0.009 inches, 0.01 inches, 0.012 inches, 0.014 inches, 0.016 inches, 0.018 inches, or 0.02 inches. For example, a size of pores on a porous filter may be equal to or lesser than about 0.0005 inches, 0.001 inches, 0.002 inches, 0.003 inches, 0.004 inches, 0.005 inches, 0.006 inches, 0.007 inches, 0.008 inches, 0.009 inches, 0.01 inches, 0.012 inches, 0.014 inches, 0.016 inches, 0.018 inches, or 0.02 inches. For example, a size of pores on a porous filter may be in between about 0.0005 inches, 0.001 inches, 0.002 inches, 0.003 inches, 0.004 inches, 0.005 inches, 0.006 inches, 0.007 inches, 0.008 inches, 0.009 inches, 0.01 inches, 0.012 inches, 0.014 inches, 0.016 inches, 0.018 inches, or 0.02 inches.

The porous element 1182 may be made from any conventionally known process. For example, the porous element may be made from powdered metal using a sintering process.

A vaporizer utilizing comprising a porous filter atomizer 1104 may mitigate risks associated with electrical shorting. For example, connections with the heating element may be made on inlet tube 1134 on one end 1184 and on another end 1186 of a coil or chamber 1116. As the coil rests on an insulated portion of tube 1134, i.e., the porous filter, there may be no risk of electrical shorting. In some instances, liquid may enter the tube 1134 and flow through filter 1182, e.g., while heating and evaporating and exiting on an open end into the chamber 1116.

Figure 12:
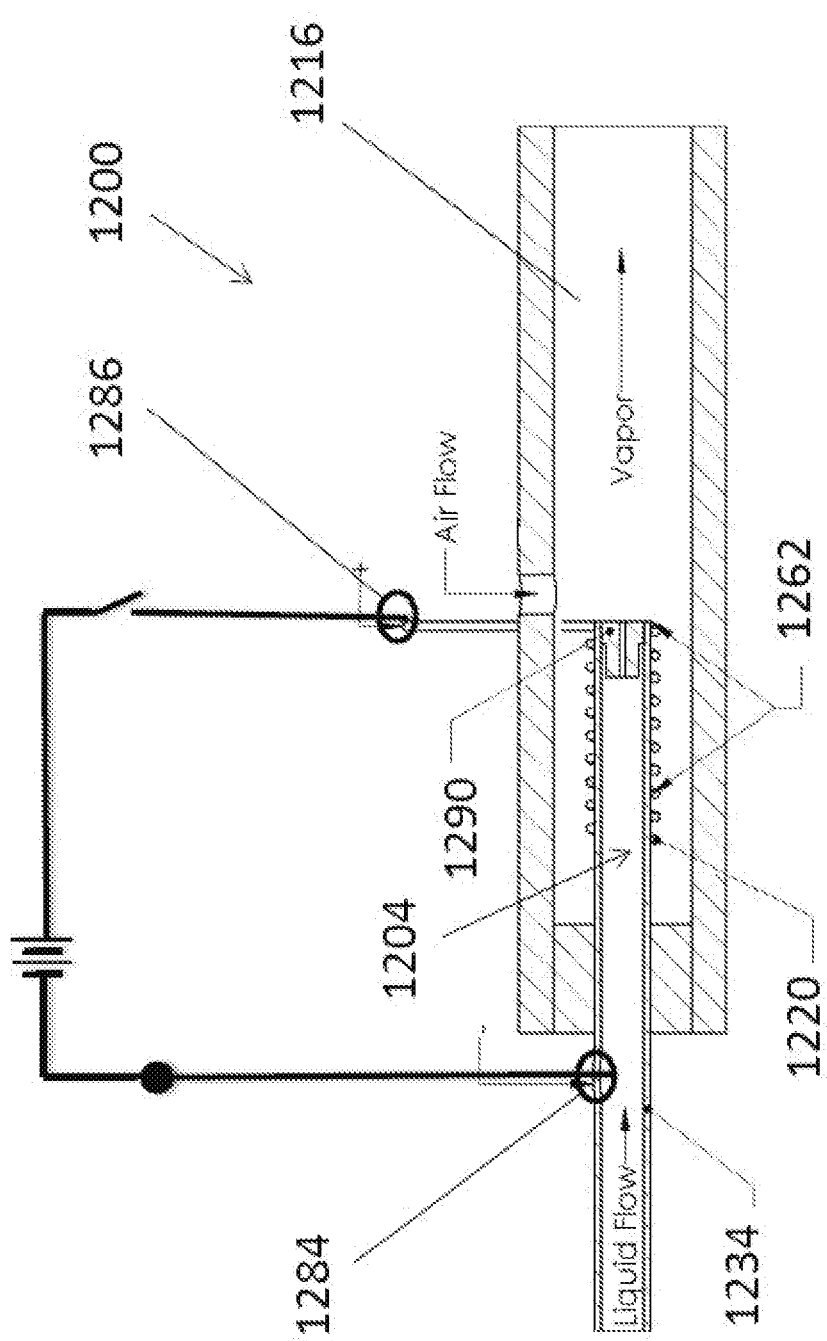
FIG. 12 illustrates a vaporizing device comprising a baffled tube atomizer, in accordance with embodiments.

FIG. 12 illustrates a vaporizing device 1200 comprising a baffled tube atomizer 1204, in accordance with embodiments. In some instances, the vaporizer 1200 may comprise the baffled tube atomizer 1204 coupled with a breath-modulated valve or any of the components described throughout, e.g., a venturi tube. The baffled tube atomizer 1204 may comprise a baffle element 1290. The baffle element 1290 may also be referred to as a baffle or baffle tube throughout. In some instances, the baffle element 1290 may be metallic. In some instances, the baffle element 1290 may be pressed into an outlet (e.g., exit, proximal end, etc.) of inlet tube 1234. In some instances, the inlet tube 1234 may be a portion of the inner elongated member previously described herein. Alternatively, the inlet tube 1234 may be an intermediary element configured to couple the heating element 1220 to an inner elongated member, substantially as described above.

In some instances, the baffle element 1290 may be configured to mitigate unevaporated liquid from entering chamber 1216. For example, a through-hole in a baffle 1290 may be sized such that vapor may escape the baffle element 1290 while unevaporated liquid may not escape. For example, a size of a through-hole on a baffle element 1290 may be equal to or greater than about 0.0005 inches, 0.001 inches, 0.002 inches, 0.003 inches, 0.004 inches, 0.005 inches, 0.006 inches, 0.007 inches, 0.008 inches, 0.009 inches, 0.01 inches, 0.012 inches, 0.014 inches, 0.016 inches, 0.018 inches, or 0.02 inches. For example, a size of a through-hole on a baffle element 1290 may be equal to or lesser than about 0.0005 inches, 0.001 inches, 0.002 inches, 0.003 inches, 0.004 inches, 0.005 inches, 0.006 inches, 0.007 inches, 0.008 inches, 0.009 inches, 0.01 inches, 0.012 inches, 0.014 inches, 0.016 inches, 0.018 inches, or 0.02 inches. For example, a size of a through-hole on a baffle may be in between about 0.0005 inches, 0.001 inches, 0.002 inches, 0.003 inches, 0.004 inches, 0.005 inches, 0.006 inches, 0.007 inches, 0.008 inches, 0.009 inches, 0.01 inches, 0.012 inches, 0.014 inches, 0.016 inches, 0.018 inches, or 0.02 inches.

In some instances, a length of the baffle element 1290 may encompass a portion of the inlet tube 1234. A length of the baffle element 1290 may encompass a portion of a heated region of the tube 1234. For example, a length of the baffle element 1290 may correspond to a portion of the tube 1234 over which a heating element resides or is coupled to. For example, a length of the baffle element 1290 may be equal to or greater than about 0.0005 inches, 0.001 inches, 0.002 inches, 0.003 inches, 0.004 inches, 0.005 inches, 0.006 inches, 0.007 inches, 0.008 inches, 0.009 inches, 0.01 inches, 0.012 inches, 0.014 inches, 0.016 inches, 0.018 inches, or 0.02 inches. For example, a length of the baffle element may be equal to or less than about 0.0005 inches, 0.001 inches, 0.002 inches, 0.003 inches, 0.004 inches, 0.005 inches, 0.006 inches, 0.007 inches, 0.008 inches, 0.009 inches, 0.01 inches, 0.012 inches, 0.014 inches, 0.016 inches, 0.018 inches, or 0.02 inches. For example, a length of the baffle element 1290 may be equal to or in between about 0.0005 inches, 0.001 inches, 0.002 inches, 0.003 inches, 0.004 inches, 0.005 inches, 0.006 inches, 0.007 inches, 0.008 inches, 0.009 inches, 0.01 inches, 0.012 inches, 0.014 inches, 0.016 inches, 0.018 inches, or 0.02 inches.

In some instances, an outside of the inlet tube 1234 may comprise an electrically insulating coating 1262 (e.g., ceramic adhesive). In some instances, the electrically insulating coating may be present on portions of the tube 1234, e.g., along a length of the baffle element 1290. In some instances, the heating element 1220, such as a heated coil, may reside over the electrical insulating coating 1262. In some instances, a portion of the coil may reside on a non-insulated tube section, while another portion of the coil may protrude from the chamber 1216. FIG. 12 presents a baffled tube atomizer configuration wherein the heater connections may be made on the tube 1234 on one end 1284 and at another end 1286 of the coil or chamber. As the coil rests on the insulated portion of the inlet tube 1234, there may be no risk of electrical shorting.

In embodiments where the heater is a coil, the wire of the coil can be coated in a temperature resistant dielectric insulator, such as polytetrafluoroethylene (PTFE), polyether ether ketone (PEEK), polyetherimide (PEI),polyimide, glass, or ceramic. The insulating coating can have a thickness between, for example, 0.1 and 20 microns. Coating the wire can further avoid electrical shorting.

In any of the variations described herein, the apparatus (vaporizer apparatus) may be configured to periodically clean the heater. A heater, including both wicked (e.g., using a wick) and wickless heater may accumulate residues or surface impurities with use. In some instances, the heater design and control loop can be specifically designed so as to ensure complete and clean evaporation of the liquid. Doing so may prevent a residue from developing on the surface of the heater over time (which can degrade vapor production, cause off-taste, and potentially release harmful degradants). As a result, the heaters described herein can function for over 6 months, such as over 9 months.

Alternatively or additionally, any of the vaporizing devices described herein may include a periodic cleaning cycle (self-cleaning) in which the heater is fired without the user puffing to burn or bake off any residue that develops on the heater over time. The vaporizing devices can include an automatic indicator to start cleaning and/or can clean automatically. Such an indication or automatic cleaning can be determined based upon a set number of puffs on the device, a certain time of usage, and/or other usage data. The schematic illustration shown in FIG. 13 illustrates an example including a controller that may optionally be configured to include a self-cleaning 1315 capability. In this example the controller 1305 may include software, hardware and/or firmware for controlling the apparatus to self-clean the heater 1335.

For example, a vaporizer may be configured to heat to a high temperature for a predetermined time period in order to clean the heater (e.g., heating coil, etc.). In some variations the cleaning temperature is greater than any of the normal operating (vaporizing) temperatures. For example, the temperature may be greater than 300° C., greater than 350° C., greater than 400° C., greater than 410° C., greater than 425°

C., greater than 430° C., greater than 440° C., greater than 450° C., greater than 475° C., greater than 500° C., greater than 525° C., greater than 550° C., etc. The predetermined cleaning timer period may be greater than 30 seconds, greater than 1 minute, greater than 2 minutes, greater than 3 minutes, greater than 4 minutes, greater than 5 minutes, greater than 6 minutes, greater than 7 minutes, greater than 8 minutes, greater than 9 minutes, greater than 10 minutes, greater than 12 minutes, greater than 15 minutes, greater than 17 minutes, etc. (e.g., between 1 minute and 10 minutes, etc.).

The apparatus may be configured so that the controller schedules and/or initiates self-cleaning when it determines that the user will not be operating the device. For example, the controller may initiates self-cleaning only when charging, and/or when the sensor(s) determine that the user is not operating the device (e.g., following a period of protracted, e.g., <30 min, without movement and/or user contact). Scheduling may be based, in part, on time of day (e.g., at off-use hours based on prior operation). In some variations, the apparatus may provide a signal or message to the user that a self-cleaning is scheduled and/or in process; the user may terminate or cancel the self-cleaning. An apparatus may notify a user by indicating on the apparatus (e.g., using a LED, display, transmission to a user device such as a cellphone, etc.).

In some embodiments, the heater can be configured to fire briefly after each user puff to ensure complete evaporation of the liquid and prevent residue from developing on the surface of the heater.

In any of the apparatuses described herein, the vaporization device can include a three-part system wherein the heater is semi-durable and is replaced periodically. The timing of the replacement can be indicated by the device, for example, based upon a set number of puffs on the device, a certain time of usage, and/or other usage data.

A vaporizing device as disclosed herein may comprise one or many components or embodiments described herein. For example, the vaporizing device may comprise a fluid flow modulator and an atomizer comprising a porous filter and a baffle element.

The present disclosure presents a method of enhanced flow control in a vaporizing device; the method comprising providing a vaporizing device, wherein said device is an electronic cigarette; optionally, configuring any of the valves previously described herein in said device; configuring said device with any of the improved atomizer designs herein previously described.

In another aspect, the present disclosure presents a method of enhanced flow control in a vaporizing device; the method comprising providing a vaporizing device, wherein said device is an electronic cigarette; configuring any of a breath-modulated elastomeric or bimetallic valve, previously described herein in said device; configuring said device with any of the improved atomizer designs herein previously described.

The present disclosure provides a method of breath-modulation control in a vaporizing device for vaporization of an organic material, the method comprising providing a vaporizing device with a breath-modulating valve, configuring the valve, as a replacement to a conventional wick, allowing flow from a reservoir into an atomizer when a user inhales from a mouthpiece of the device. The present disclosure provides embodiments of improved atomizer designs for vaporizing devices, where said designs can be configured optionally, with various embodiments of a breath-modulating valve incorporated in a vaporizing device to replace a conventional wick. In some instances, the vaporizing device may be an electronic cigarette.

The vaporizing devices described herein, e.g., the wick-less vaporizing devices, may have a plurality of advantages as compared to conventional vaporizing devices. For example, the vaporizers described herein may enable production of vaporizers that are efficient and/or produce a high quality vapor. For example, the vaporizing device of the present disclosure may eliminate issues associated with cooked or burnt flavor, flooding or gurgling, leaking, dislodging of an elongated member, sedimentation build up, flavor cross-over, short battery life, and/or poor user experience in general. For example, a using a power equivalent to those used by a conventional vaporizer, the vaporizer of the present disclosure may produce a flow rate that is at least 1.2 times, 1.5 times, 2 times, 2.5 times, 3 times, 3.5 times, 4 times, 5 times, 6 times, 8 times, or 10 times that of a conventional vaporizer.

With the improvements herein disclosed, in some instances, changes in environmental pressure or temperature (e.g., going from indoors to outdoors, being in the cabin of a commercial airliner, etc.) may not result in oversaturation or leakage of the inner elongated member. In some instances, the inner elongated member of the vaporizer may not be subject to dislodgement. A dislodgement of the inner elongated member may render a vaporizer non-functional. In some instances, a dislodged inner elongated member may come in direct contact with a user's lips, palate and/or tongue, resulting in an unpleasant and unclean experience. In some instances, the vaporizer may not become flooded (e.g., gurgled, gurgling, etc.) over time or a after a period of use. In some instances, sedimentation of solids that are in suspension in the liquid (e.g., within a liquid reservoir) may not result. In some instances, the inner elongated member of the vaporizer may not be subject to drying and vapor produced by the vaporizer may not overheat and/or acquire a burnt taste even after repeated use. In some instances, products formed (e.g., degradation products) during vaporization may not be transported or leech into the reservoir, e.g., due to the fluid flow modulator. For example, there may be no medium on which degradation products can accumulate on. In some instances, there may be no medium on which different liquid solutions with different flavors and/or chemical formulas may accumulate or remain on. In some instances, there may be no extraneous mass that needs to be heated and cooled (e.g., repeatedly) along with a liquid solution in vaporizing the liquid. The necessity to heat and cool additional elements may result in wasted energy (e.g., from the battery source) and may limit a number of cycles that may be drawn (e.g., puff from a user, vaporization, etc.) on a single charge.

An ability to modulate or control a fluid flow may give rise to the aforementioned advantages.

The herein described subject matter sometimes illustrates steps that are different, varying with the different components contained within, or connected with, different other components in a vaporizing device. It is to be understood that the configurations and/or components disclosed herein are merely exemplary, and that in fact many other components can be implemented which achieve the same functionality.

As used herein, the term "about" may refer to an amount within +/−1, 2, 3, 4, 5, 6, 7, 8, 9, or 10% of a subsequently mentioned value. For example, an airflow rate of about 100 L/min may also refer to an airflow rate of 101, 102, 103, 104, 105, 106, 107, 108, 109, or 110 L/min.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Any components disclosed herein may be "associated with" each other such that the desired functionality is achieved, irrespective of architectures or intermedial components. Likewise, any components so associated can also be viewed as being "operably connected", or "operably coupled", to each other to achieve the desired functionality, and any components capable of being so associated can also be viewed as being "operably couplable" to each other to achieve the desired functionality. For example, operably couplable components include but are not limited to physically mateable and/or physically interacting components and/or wirelessly interactable and/or wirelessly interacting components and/or logically interacting and/or logically interactable components.

In this disclosure, a start of the aerosolization of the organic formulation can be the actual use of the vaporizing device, which can be designated as a user puffing on the vaporizing device, and/or taking a drag on the aerosolized formulation.

Heat may be generated in the electronic cigarette through ohmic heating. In ohmic heating a current may be passed through an electrically resistive material to generate heat that can be transmitted to an adjacent article. This mode of heat production has been employed to vaporize or heat a volatile substance, for example tobacco, for inhalation by a user. Cigarette holders and pipe bowls having an electrical resistance coil to generate heat in order to volatilize tobacco flavors and of drugs other than tobacco by ohmic heating have been previously described. Ohmic heating can facilitate precise control of energy applied to determine the heat generated. In some cases ohmic heating systems may be associated with delays on an order of seconds or minutes between a time heating is initiated and a time when maximum temperature is achieved. The delays may be especially relevant for small systems where energy available is limited (e.g., when using batteries).

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Within this written description, the particular naming of the components, capitalization of terms, the attributes, data structures, or any other programming or structural aspect is not mandatory or significant, and the mechanisms that implement the present disclosure or its features may have different names, formats, or protocols. Further, the breath-modulated assembly may be implemented via a combination of hardware and software, as described, or entirely in hardware elements. Also, the particular division of functionality between the various system components described herein is merely exemplary, and not mandatory; functions performed by a single system component may instead be performed by multiple components, and functions performed by multiple components may instead be performed by a single component.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

It should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention. Having described the present disclosure above, various modifications of the techniques, procedures, material and equipment will be apparent to those in the art. It is intended that all such variations within the scope and spirit of the appended claims be embraced thereby.

The foregoing examples illustrate various aspects of the present disclosure and practice of the methods of the present disclosure. The examples are not intended to provide an exhaustive description of the many different embodiments of the present disclosure. Thus, although the foregoing present disclosure has been described in some detail by way of illustration and example for purposes of clarity and understanding, those of ordinary skill in the art will realize readily that many changes and modifications may be made thereto without departing form the spirit or scope of the present disclosure.

Unless otherwise indicated, all numbers expressing quantities and conditions, and so forth used in the specification and claims are to be understood as being modified in all instances by the term "about." The terminology used herein is for the purpose of describing particular embodiments only and is not intended to be limiting of the present disclosure. As used herein, the singular forms "a," "an," and "the" are intended to include the plural forms as well, unless the context clearly indicates otherwise. It will be further understood that the terms "comprises," "comprising," "includes," and/or "including" when used in this specification, specify the presence of stated features, integers, steps, operations, elements, and/or components, but do not preclude the presence or addition of one or more other features, integers, steps, operations, elements, components, and/or groups thereof.

The present disclosure is described below with reference to block diagrams and/or flowchart illustrations of methods, apparatus (systems and/or devices) and/or computer program products according to embodiments of the present disclosure. It is understood that a block of the block diagrams and/or flowchart illustrations, and combinations of blocks in the block diagrams and/or flowchart illustrations, may be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means (functionality) and/or structure for implementing the functions/acts specified in the block diagrams and/or flowchart block or blocks.

What is claimed is:

1. A vaporizer comprising:
   an elongate body;
   a reservoir configured to contain a vaporizable fluid;
   an atomizer within the elongate body, the atomizer configured to heat the vaporizable fluid to generate an aerosol, the atomizer comprising a heating element;
   a tube extending between the reservoir and the heating element, the tube configured to permit a bulk flow of the vaporizable fluid from the reservoir to the heating element;
   a flow modulator configured to modulate the bulk flow of the vaporizable fluid through the tube from the reservoir to the heating element;
   a mouthpiece;
   a draw sensor configured to detect a user drawing on the mouthpiece;
   a controller configured to control the flow modulator to permit the bulk flow of the vaporizable fluid when the user is drawing on the mouthpiece;
   a cartridge; and
   a battery unit, wherein the cartridge is configured to removably couple with the battery unit, and wherein the reservoir is part of the cartridge and the battery unit comprises the atomizer.

2. The vaporizer of claim 1, wherein a primary means of vaporizable fluid transportation through the tube is not via capillary action.

3. The vaporizer of claim 1, wherein the flow modulator comprises a valve.

4. The vaporizer of claim 1, wherein the flow modulator comprises a deformer.

5. The vaporizer of claim 4 wherein the deformer is elastic.

6. The vaporizer of claim 4 wherein the deformer comprises a spring.

7. The vaporizer of claim 4 wherein the deformer comprises an elastomeric membrane.

8. The vaporizer of claim 4 wherein the deformer comprises bi-metallic composite configured to curl or flex along one or more axis in response to a stimuli.

9. The vaporizer of claim 8 wherein the stimuli is heat.

10. The vaporizer of claim 4 wherein a deformation of the deformer causes the flow modulator to open and close.

11. The vaporizer of claim 4 wherein the deformer comprises a resting state.

12. The vaporizer of claim 11 wherein in the resting state, the deformer prevents flow of the vaporizable fluid through the tube.

13. The vaporizer of claim 1 wherein the atomizer is wickless.

14. The vaporizer of claim 1 wherein the heating element includes a coil.

15. The vaporizer of claim 1 wherein the heating element is at least partially wound around the tube.

16. The vaporizer of claim 1 wherein the heating element is a resistive heater.

17. The vaporizer of claim 1 further comprising a chamber configured to permit vapor to pass therethrough for inhalation by the user.

18. The vaporizer of claim 17, wherein a configuration of the flow modulator depends on a degree of vacuum applied to the chamber.

19. The vaporizer of claim 1 wherein the tube comprises one or more vent slots.

20. The vaporizer of claim 19 wherein the one or more vent slots are configured to permit the vaporizable fluid to flow therethrough.

21. The vaporizer of claim 1 wherein the tube includes a diffusor configured to mix vapor and air.

22. The vaporizer of claim 17 wherein the tube includes a baffle configured to release vapor into the chamber but retain an unvaporized portion of the vaporizable fluid within the atomizer.

23. The vaporizer of claim 17 wherein the atomizer comprises a baffle configured to release the vapor within the chamber but retain an unvaporized portion of the vaporizable fluid within the atomizer.

24. The vaporizer of claim 22 wherein the baffle comprises one or more through-holes.

25. The vaporizer of claim 24 wherein the through-holes are equal to or less than about 0.01 inches.

26. The vaporizer of claim 25 wherein the through-holes are equal to or less than about 0.006 inches.

27. The vaporizer of claim 1 wherein the tube comprises a porous filter configured to release vapor for inhalation but retain an unvaporized portion of the vaporizable fluid within the atomizer.

28. The vaporizer of claim 1 wherein the atomizer comprises a porous filter configured to release vapor for inhalation but retain an unvaporized portion of the vaporizable fluid within the atomizer.

29. The vaporizer of claim 27 wherein the porous filter comprises one or more pores.

30. The vaporizer of claim 29 wherein a substantial portion of the one or more pores are equal to or less than about 0.01 inches.

31. The vaporizer of claim 29 wherein an average size of the one or more pores are equal to or less than about 0.01 inches.

32. The vaporizer of claim 29 wherein a substantial portion of the one or more pores are equal to or less than about 0.006 inches.

33. The vaporizer of claim 29 wherein an average size of the one or more pores are equal to or less than about 0.006 inches.

34. The vaporizer of claim 1 further comprising one or more processors configured to activate the atomizer in response to an inhalation of a user.

35. The vaporizer of claim 1 further comprising a fluid pump configured to actively pump the vaporizable fluid through the tube.

36. The vaporizer of claim 1 further comprising a venturi tube configured to create an amplified vacuum within a throat of the venturi tube in response to an inhalation of a user.

37. A method of providing an inhalable aerosol, the method comprising:

sensing a user draw through a mouthpiece of a vaporizer apparatus;

controlling, via a flow modulator, flow of a vaporizable fluid from a reservoir of the vaporizer apparatus through a tube to a heater;

heating, based on sensing the user draw, the heater to vaporize the vaporizable fluid to generate the inhalable aerosol; and providing through the mouthpiece, the inhalable aerosol into the user draw, wherein the reservoir is part of a removable cartridge configured to couple with a battery unit that comprises the heater.

38. The method of claim 37 further comprising:

stopping flow through the tube by the flow modulator when the user is no longer drawing through the mouthpiece.

* * * * *